US012698288B2

(12) United States Patent
Nam et al.

(10) Patent No.: US 12,698,288 B2
(45) Date of Patent: Aug. 4, 2026

(54) COMPOUNDS HAVING CYCLIN-DEPENDENT KINASE(CDK)-INHIBITORY FUNCTION

(71) Applicant: QURIENT CO., LTD., Gyeonggi-do (KR)

(72) Inventors: Kiyean Nam, Gyeonggi-do (KR); Jaeseung Kim, Seoul (KR); Dongsik Park, Gyeonggi-do (KR); Mooyoung Seo, Gyeonggi-do (KR); Yeejin Jeon, Gyeonggi-do (KR); Donghoon Yu, Gyeonggi-do (KR)

(73) Assignee: QURIENT CO., LTD, Gyeonggi-Do (KR)

( * ) Notice: Subject to any disclaimer, the term of this patent is extended or adjusted under 35 U.S.C. 154(b) by 384 days.

(21) Appl. No.: 18/036,102

(22) PCT Filed: Nov. 29, 2021

(86) PCT No.: PCT/EP2021/083368

§ 371 (c)(1),
(2) Date: May 9, 2023

(87) PCT Pub. No.: WO2022/117504

PCT Pub. Date: Jun. 9, 2022

(65) Prior Publication Data

US 2025/0263413 A1 Aug. 21, 2025

Related U.S. Application Data

(60) Provisional application No. 63/120,459, filed on Dec. 2, 2020.

(51) Int. Cl.

| | |
|---|---|
| ***C07D 487/04*** | (2006.01) |
| ***A61K 31/53*** | (2006.01) |

(Continued)

(52) U.S. Cl.
CPC ............ *C07D 487/04* (2013.01); *A61K 31/53* (2013.01); *A61K 31/675* (2013.01); *A61P 35/00* (2018.01); *C07F 9/6561* (2013.01)

(58) Field of Classification Search
CPC ....... C07D 487/04; A61P 35/00; A61K 31/53; A61K 31/675
(Continued)

(56) References Cited

U.S. PATENT DOCUMENTS

| | | | | |
|---|---|---|---|---|
| 1,858,937 A * | 5/1932 | Pointon | A61K 31/519 | 487/4 |
| 8,658,639 B2 * | 2/2014 | Suetsugu | A61K 31/538 | 514/230.5 |
| 11,858,937 B2 * | 1/2024 | Nam | A61K 31/519 | 487/4 |

FOREIGN PATENT DOCUMENTS

| | | | |
|---|---|---|---|
| EP | 1 908 761 A1 * | 4/2008 | C07D 413/12 |
| WO | WO 2006/005741 A2 * | 1/2006 | C07D 413/14 |

(Continued)

*Primary Examiner* — Jeffrey S Lundgren
*Assistant Examiner* — Heather Dahlin
(74) *Attorney, Agent, or Firm* — SALIWANCHIK, LLOYD & EISENSCHENK

(57) ABSTRACT

The present invention relates to compounds having cyclin-dependent kinase (CDK)-inhibitory functions and/or pharmaceutically acceptable salts thereof, the use of these compounds as pharmaceutically active agents, especially for the prophylaxis and/or treatment of cell proliferative diseases, inflammatory diseases, immunological diseases, cardiovascular diseases and infectious diseases. Furthermore, the present invention is directed towards pharmaceutical compositions containing such compounds.

16 Claims, 2 Drawing Sheets

(51) Int. Cl.

| | |
|---|---|
| ***A61K 31/675*** | (2006.01) |
| ***A61P 35/00*** | (2006.01) |
| ***C07F 9/6561*** | (2006.01) |

(58) Field of Classification Search

USPC ............................................................ 514/81

See application file for complete search history.

(56) References Cited

FOREIGN PATENT DOCUMENTS

| | | | | |
|---|---|---|---|---|
| WO | 2019/197549 A1 | | 10/2019 | |
| WO | WO 2019/197546 A1 | * | 10/2019 | ........... C07D 487/04 |

* cited by examiner

In-vivo efficacy results of selected compounds of present invention in A2780 CDX model
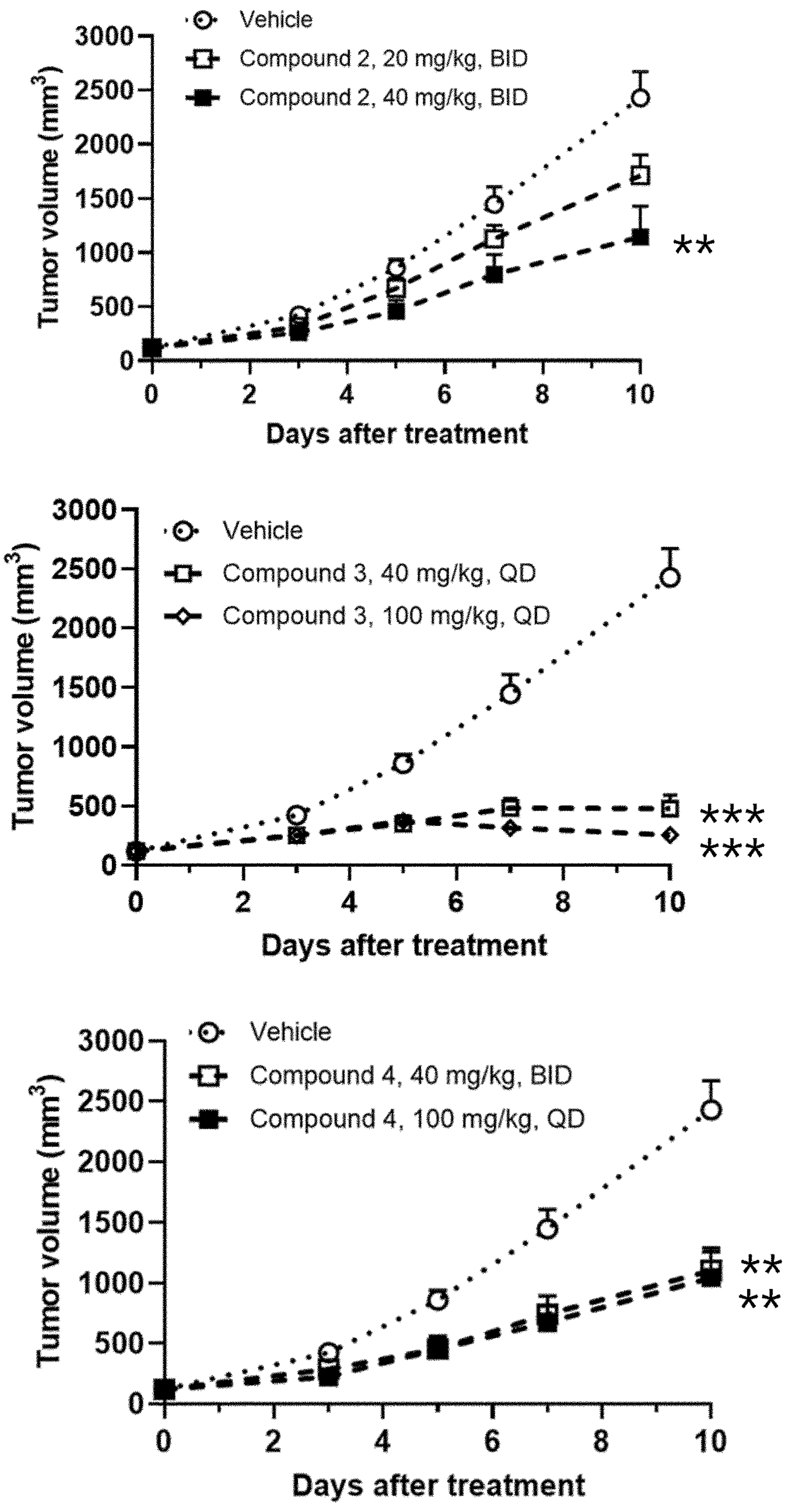

continued
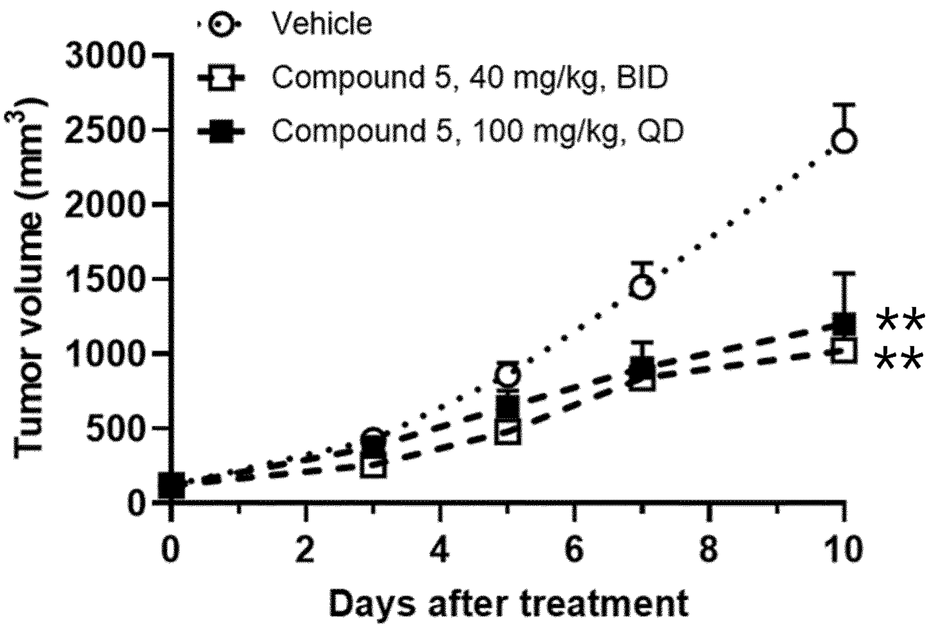
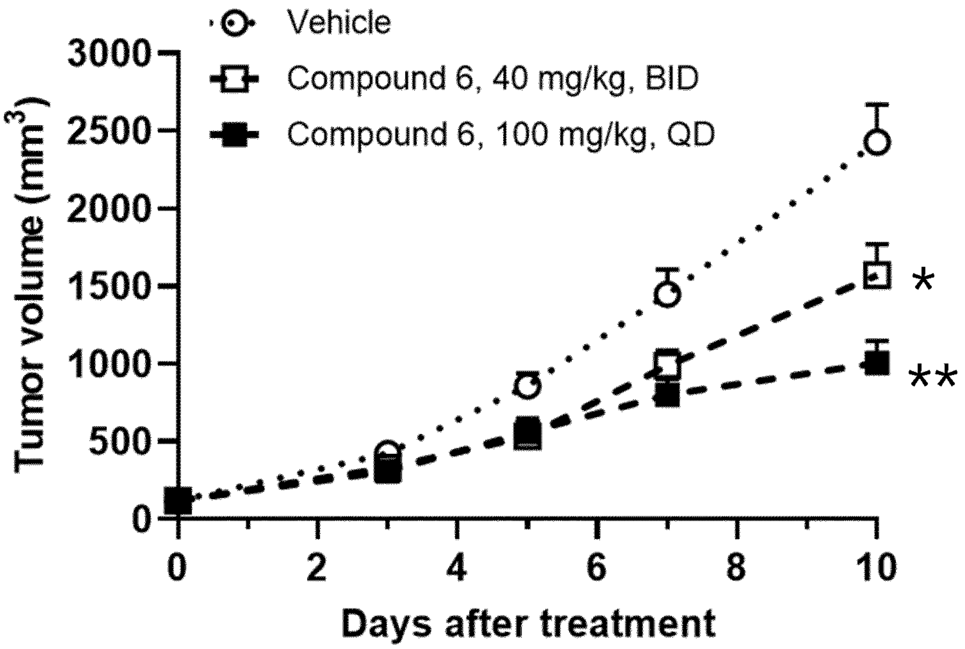
One-way ANOVA, * *p<0.01* ** *p<0.001* *** *p<0.0001* compared to vehicle

COMPOUNDS HAVING CYCLIN-DEPENDENT KINASE(CDK)-INHIBITORY FUNCTION

CROSS REFERENCE TO RELATED APPLICATIONS

This application is a National Stage Application of International Application Number PCT/EP2021/083368, filed Nov. 29, 2021; which claims the benefit of U.S. Provisional Application Ser. No. 63/120,459, filed Dec. 2, 2020, both of which are incorporated herein by reference in their entirety.

FIELD OF THE INVENTION

The present invention relates to compounds having cyclin-dependent kinase (CDK)-inhibitory functions and/or pharmaceutically acceptable salts thereof, the use of these compounds as pharmaceutically active agents, especially for the prophylaxis and/or treatment of cell proliferative diseases, inflammatory diseases, immunological diseases, cardiovascular diseases and infectious diseases. Furthermore, the present invention is directed towards pharmaceutical compositions containing such compounds.

BACKGROUND OF THE INVENTION

Cyclin-dependent kinase (CDK) family members that trigger passage through the cell cycle are being considered as attractive therapeutic targets, especially for cancer. CDK family members that control other processes such as transcription and RNA processing have caught less attention so far, although experimental evidence for their involvement in different pathological processes is emerging. Together with cell cycle control, CDK/cyclin complexes also have been identified as conserved components of the RNA polymerase II (Pol II) transcriptional machinery (Bregman et al., 2000, *Front Biosci.* 5:244-257). There are currently 20 known mammalian CDKs. While CDK7-13 have been linked to transcription, only CDK 1, 2, 4, and 6 show demonstrable association with cell cycle. Unique among the mammalian CDKs, CDK7 has consolidated kinase activities, regulating both the cell cycle progression and transcription (Desai et al., 1995, Mol. Cell Biol. 15, 345-350).

The general transcription factor TFIIH purified from mammalian cells consists of ten subunits, seven of which (p62, p52, p44, p34, XPD, XPB, and TTDA) form the core complex. Three subunits (cyclin H, MAT1, and CDK7) from the CDK-activating kinase (CAK), which is linked to TFIIH's core via the XPD (ATP-dependent helicase) subunit of complex. During the process of transcription initiation, the helicase activity of TFIIH opens the core promoter DNA, while CDK7 phosphorylates the C-terminal domain (CTD) of Pol II at serine 5 and 7 (Akhtar et al., 2009, Mol. Cell 34, 387-393) as well as other transcription factors controlling the initiation-to-elongation transition (Larochelle et al., 2012, Nat. Strut. Mol. Biol. 19, 1108-1115 Therefore CDK7 is essential factor for transcription process, which suggests that CDK7 is a target for cancer therapy, especially transcription addicted cancer.

CDK7 has long been asserted as having an essential role in cellular metabolism and viability. Transcriptional CDK inhibitors down-regulate a large number of short-lived anti-apoptotic proteins, such as the anti-apoptotic proteins myeloid cell leukemia-1 (Mcl-1), B-cell lymphoma extra-long (Bcl-xL) and XIAP (X-linked IAP), D-cyclins, c-Myc, Mdm-2 (leading to p53 stabilization), p21$^{waf1}$ proteins whose transcription is mediated by nuclear factor-kappa B (NF-kB) and hypoxia-induced VEGF (Shapiro GI. 2006, J Clin Oncol; 24(11):1770-83). The transcriptional non-selective cyclin-dependent kinase inhibitor flavopiridol induces apoptosis in multiple myeloma cells through transcriptional repression and down-regulation of Mel-1. These findings supported previous postulates that CDK7 might be a valuable target for drugs directed toward the treatment of malignancies and cell cycle-associated diseases (Lolli G and Johnson LN. 2005. *Cell Cycle* 4:572-577).

The function of CDK7 as regulator of general transcription and CDK7 is a therapeutic target for treatment of many diseases and syndromes are associated with mutations in regulatory regions and in transcription factors, cofactors, chromatin regulators and noncoding RNAs. These mutations can contribute to cancer, autoimmunity, neurological disorders, developmental syndromes, diabetes, cardiovascular disease, and obesity, among others. Some transcription factors control RNA polymerase II pause release and elongation and, when their expression or function is altered, can produce aggressive tumor cells (c-Myc) or some forms of autoimmunity (AIRE) (Tong Ihn Lee and Richard A. Young, *Cell,* 2013, 152:1237-1251). Therefore, inhibition of human CDK7 kinase activity is likely to result in anti-proliferative activity through the function in cell cycle progression and transcriptional regulation by inhibition of some transcription factor related to oncogene through inhibition of general transcription process. More important thing is that CDK7 has been shown to regulate exponential expression of oncogenic transcription factors more dramatically than it does to other housekeeping genes in cancer cells. Thus Inhibition of CDK7 can differentially affect transcription of certain oncogenes and housekeeping gene, therefore therapeutic window can be secured. For this reason, transcriptional regulation and pharmacological inhibition through appropriate general transcription inhibition by CDK7 could be applied to treat proliferative disorder, including cancer. As a general regulator of transcription, CDK7 is a therapeutic target for treatment of disease like inflammation, virus replication such as HIV, EBV, cancer and cardiac hypertrophy.

HIV-1 gene expression is regulatory by a viral transactivator protein (Tat) which induces transcriptional elongation of HIV-1 long tandem repeat. This induction requires hyperphosphorylation of the C-terminal domain repeat of RNA polymerase II. To archives said hyperphosphorylation, Tat stimulates CTD kinases associated with general transcription factors of the promoter complex, specifically TFIIH-associated CDK7 (Nekhai et al.; Biochem J. (2002) 364, 649-657). The inventors of US 615968 also described that Tat binds to CDK7 and that this interaction increase the ability of CAK to phosphorylate CTD. The authors of US 615968 further disclose that the transcriptional activation by Tat is dependent upon the kinase activity of CDK7. Additionally, Young Kyeung Kim and colleagues conclude that the recruitment and activation of TFIIH represents a rate-limiting step for the emergence of HIV from latency (Young Kyeung Kim, EMBO (2006) 25, 3596-3604).

Levels of CDK7 and CDK9, as well as other components of the kinase complexes, MAT-1/cyclin H are upregulated during Human cytomegalovirus infection. In addition, there is an increase in the kinase activities of CDK7 and CDK9 (Tamrakar et al., Journal of Virology, 2005, 79; 15477-15493).

Many antiviral drugs target viral proteins. These have the disadvantage that viruses often develop resistance against these drugs. Antiviral drugs targeting cellular proteins essential for viral process, like CDK7, could bypass this disadvantage. These drugs may further be effective in treating several unrelated viruses and their effects should be additive to traditional antiviral agents. Inhibitors of CDK7, which has its dual function of CDK-activating kinase and transcription regulation is very effective in the treatment of several viruses.

WO2019/197546 discloses inhibitors of cyclin-dependent kinases, in respect of which however, no particular administration route is described. Some of the known inhibitors of cyclin-dependent kinases are hampered by displaying a relatively low bioavailability when being administered.

BRIEF SUMMARY

Accordingly, it was an object of the present invention to provide for improved cyclin-dependent kinase-inhibitors. In particular, it was an object of the present invention to provide for cyclin-dependent kinase-inhibitors that are suitable to be formulated for oral administration.

These and other objects are solved by compounds in accordance with the present invention as well as uses of such compounds as outlined in the appended claims.

DETAILED DISCLOSURE

In one aspect, the present invention relates to a compound having the general formula I Formula I

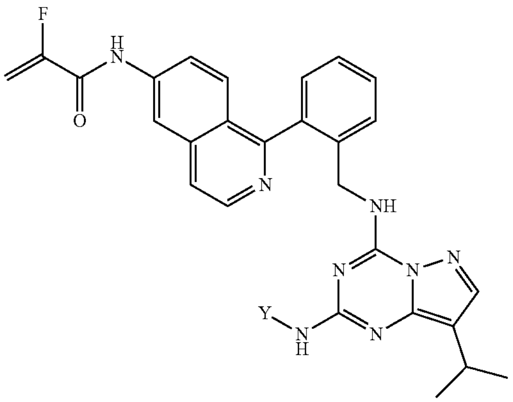

wherein

Y is, at each occurrence, independently selected from

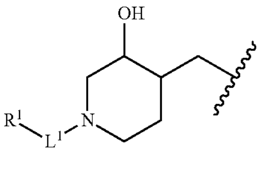

and

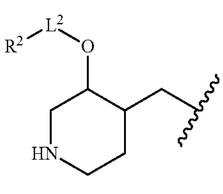

;

$L^1$ and $L^2$ are, at each occurrence, independently selected from the group consisting of $—CH_2—$, $—CH(CH_3)—$, —(C═O)—, —(C═O)NH—, —(C═O)O—, $—(C═O)OCH_2—$, $—(C═O)OCH(CH_3)—$, $—(C═O)CH_2—$, $—(C═O)CH_2C(CH_3)_2—$, $—O(SO_2)OCH_2C(CH_3)_2—$, —P(═O)OH— and $—C(CH_3)═CH—$; or $L^1$ is absent;

$R^1$ is, at each occurrence, independently selected from the group consisting of —OH, $—O(C═O)R^3$, —O(C═O)$OR^3$, $—(C═O)R^3$, aryl substituted with $—NO_2$ or $—N_3$, and any structure of the following Group A;

Group A

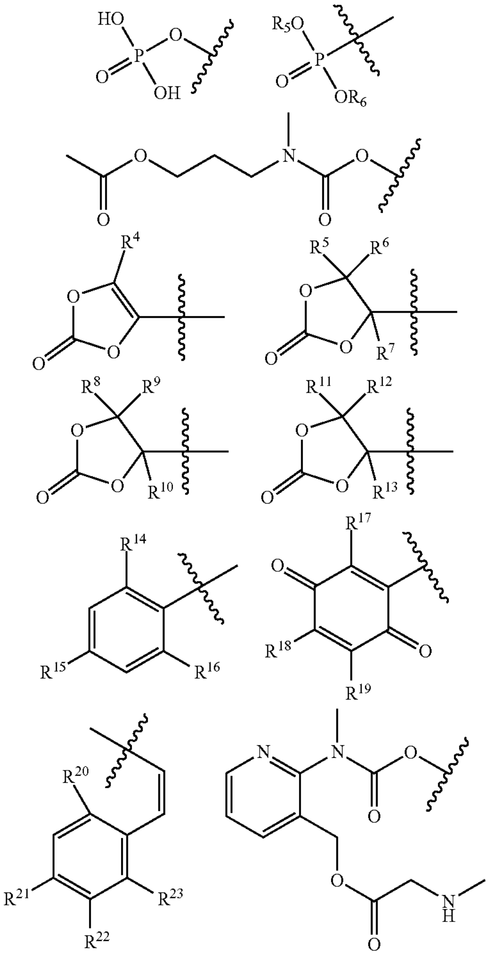

Wherein $L^1$ is only absent if $R_1$ is

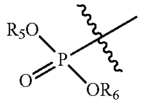

;

$R^2$ is, at each occurrence, independently selected from the group consisting of —OH, $—O(C═O)R^{24}$, $—NR^{25}R^{26}$, C1-C11 alkyl, C1-C6 alkyl substituted with —OH, —(C═O)OH or $NH_2$, heterocyclyl substituted with heterocycle, and any structure of the following Group B;

Group B

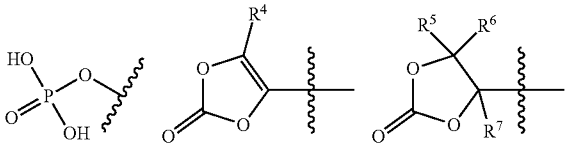

-continued

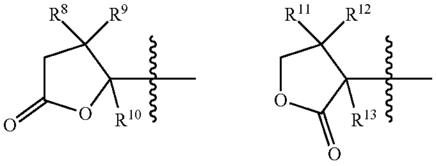

$R^3$ is, at each occurrence, independently selected from the group consisting of C1-C6 alkyl, C1-C6 alkyl substituted with alkoxy, and C3-C10 cycloalkyl;

$R^4$ is, at each occurrence, independently selected from the group consisting of C1-C3 alkyl, phenyl, phenyl substituted with C1-C3 alkyl and phenyl substituted with C1-C3 alkoxy;

$R^5$, $R^6$, $R^7$, $R^8$, $R^9$, $R^{10}$, $R^{11}$, $R^{12}$ and $R^{13}$ are, at each occurrence, independently selected from hydrogen and C1-C6 alkyl;

$R^{14}$ and $R^{20}$ are, at each occurrence, independently selected from the group consisting of hydrogen, —O(C═O)$R^{27}$, and —$NO_2$;

$R^{15}$, $R^{16}$, $R^{17}$, $R^{18}$, $R^{19}$, $R^{21}$, $R^{22}$ and $R^{23}$ are, at each occurrence, independently selected from the group consisting of hydrogen, C1-C6 alkyl, —$NO_2$, and —$N_3$;

$R^{24}$ is, at each occurrence, independently selected from the group consisting of C1-C6 alkyl and C3-C10 cycloalkyl;

$R^{25}$, $R^{26}$ and $R^{27}$ are C1-C6 alkyl;

or an enantiomer, stereoisomeric form, mixture of enantiomers, diastereomer, mixture of diastereomer, racemate of the above mentioned compounds or a pharmaceutically acceptable salt thereof.

In one embodiment of such compound(s),

Y is

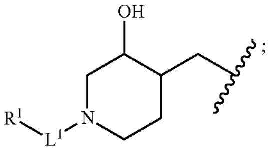

Wherein $L^1$ and $R^1$ are as defined above;

Wherein also this embodiment includes enantiomers, stereoisomeric forms, mixtures of enantiomers, diastereomers, mixtures of diastereomers, racemates of the above mentioned compounds or pharmaceutically acceptable salts thereof.

In one embodiment of such compound(s), Y is

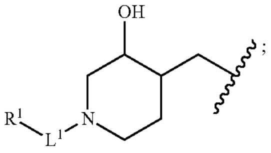

$L^1$ is as defined above; and $R^1$ is, at each occurrence, independently selected from the group consisting of —O(C═O)$R^3$, aryl substituted with —$NO_2$ or —$N_3$ and any structure of the following Group C;

Group C

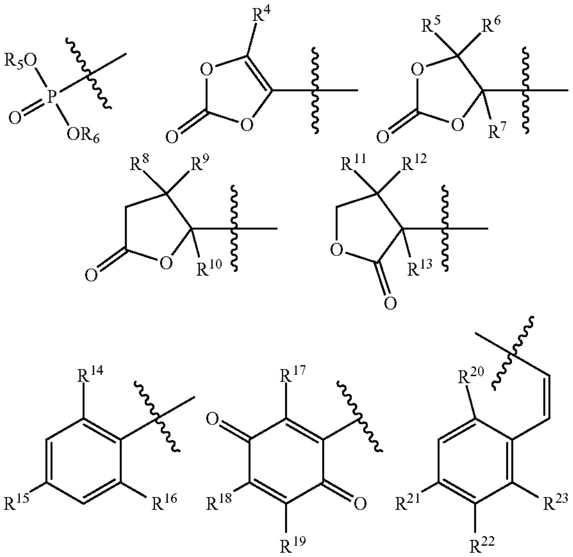

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are as defined further above;

Wherein also this embodiment includes enantiomers, stereoisomeric forms, mixtures of enantiomers, diastereomers, mixtures of diastereomers, racemates of the above mentioned compounds or pharmaceutically acceptable salts thereof.

In one embodiment of such compound,

Y is

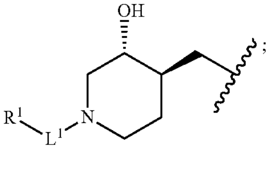

$L^1$ is, at each occurrence, independently selected from the group consisting of —$CH_2$— and —(C═O)$OCH_2$—;

$R^1$ is any structure of the following Group D;

Group D

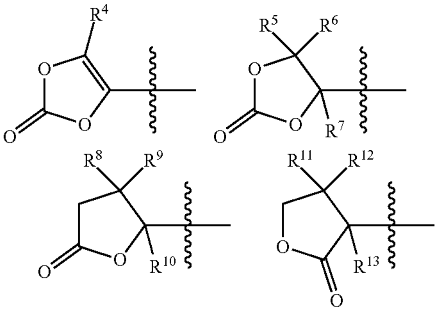

is wherein $R^4$, $R^5$, $R^6$, $R^7$, $R^8$, $R^9$, $R^{10}$, $R^{11}$, $R^{12}$ and $R^{13}$ are as defined further above;

Wherein also this embodiment includes enantiomers, stereoisomeric forms, mixtures of enantiomers, diastereomers, mixtures of diastereomers, racemates of the above mentioned compounds or pharmaceutically acceptable salts thereof.

In one embodiment of such compound(s),

Y is

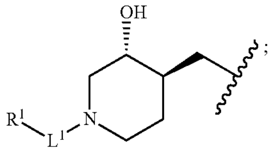

$L^1$ is, at each occurrence, independently selected from the group consisting of —$CH_2$— and —(C═O)$OCH_2$—;

$R^1$ is

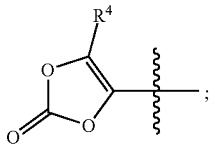

$R^5$ is as defined further above;

Wherein also this embodiment includes enantiomers, stereoisomeric forms, mixtures of enantiomers, diastereomers, mixtures of diastereomers, racemates of the above mentioned compounds or pharmaceutically acceptable salts thereof.

In one embodiment of such compound,

Y is

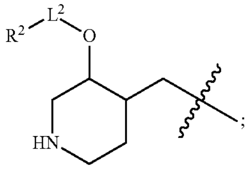

$L^2$ is —(C═O)—;

$R^2$ is, at each occurrence, independently selected from the group consisting of —O(C═O)$R^{24}$, —$NR^{25}R^{26}$, C1-C11 alkyl, C1-C6 alkyl substituted with —(C═O)OH and $NH_2$, and any structure of the following Group E;

Group E

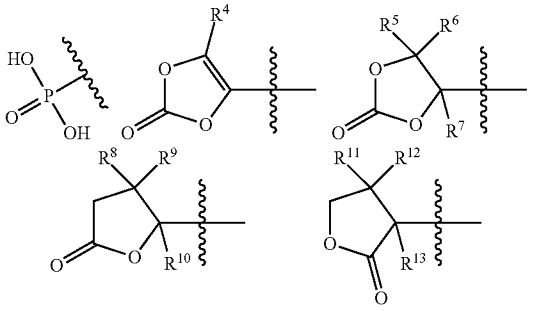

wherein $R^4$, $R^5$, $R^6$, $R^7$, $R^8$, $R^9$, $R^{10}$, $R^{11}$, $R^{12}$, $R^{13}$, $R^{24}$, $R^{25}$ and $R^{26}$ are as defined further above;

Wherein also this embodiment includes enantiomers, stereoisomeric forms, mixtures of enantiomers, diastereomers, mixtures of diastereomers, racemates of the above mentioned compounds or pharmaceutically acceptable salts thereof.

In one embodiment of such compound, said compound is any one of the compounds 1-20, as defined in the following table:

| No. | Compound |
| --- | --- |
| 1 | 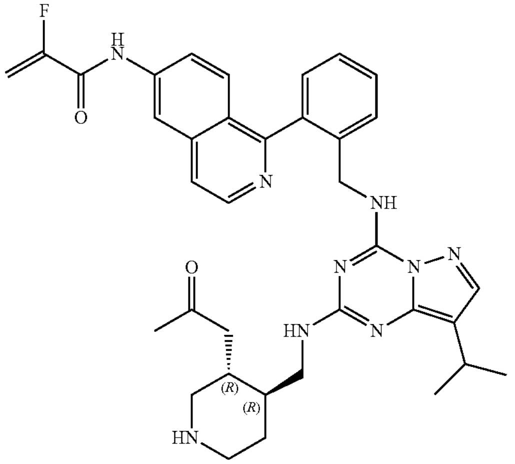 |
| 2 | 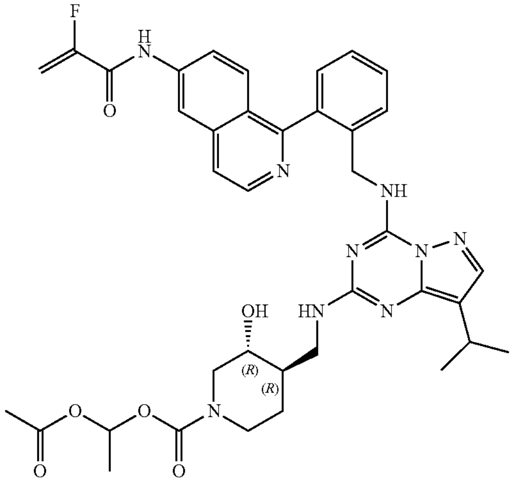 |

-continued
| No. | Compound |
| --- | --- |
| 3 | 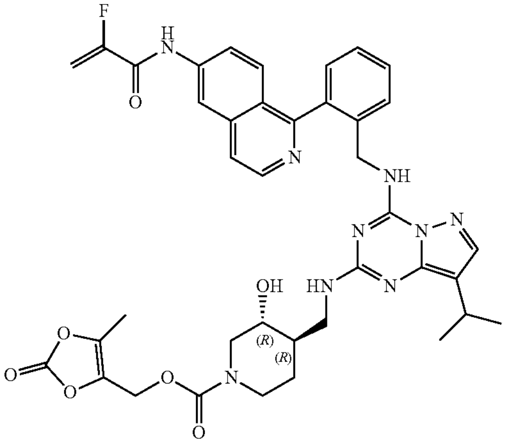 |
| 4 | 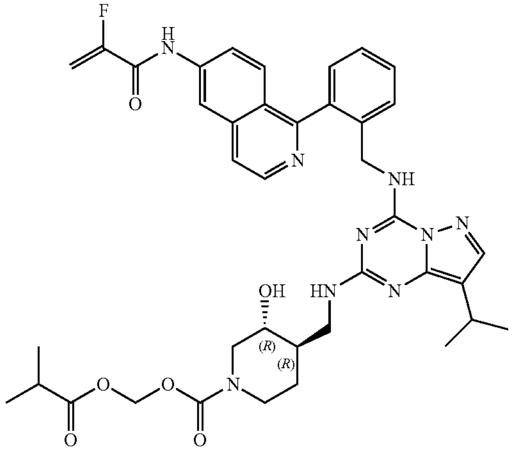 |
| 5 | 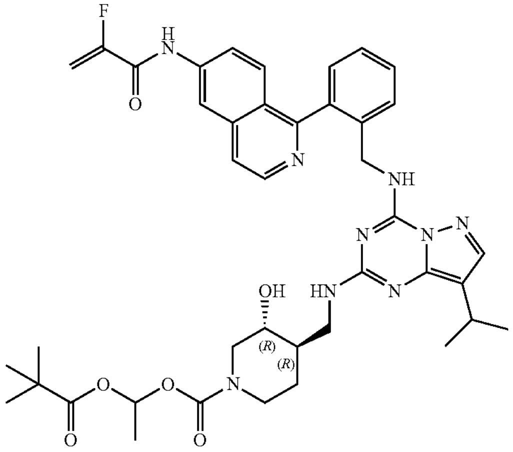 |
-continued
| No. | Compound |
| --- | --- |
| 6 | 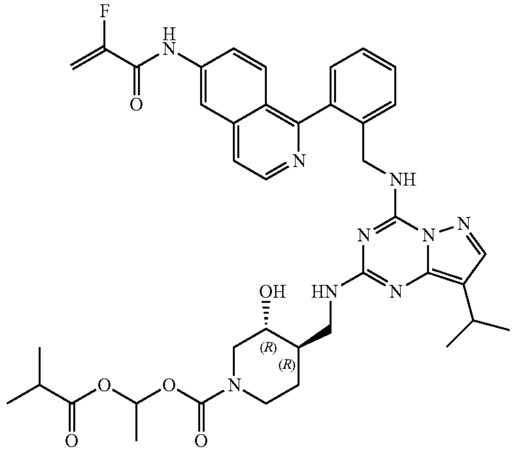 |
| 7 | 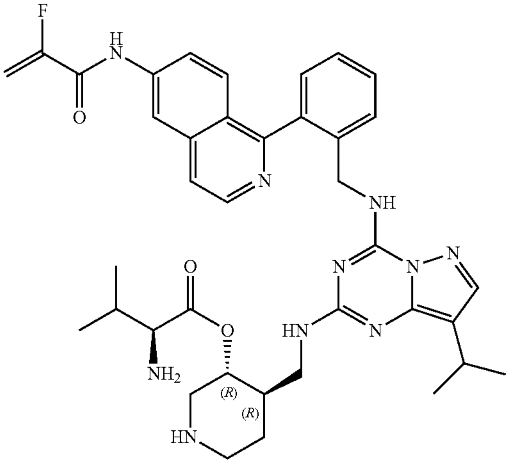 |
| 8 | 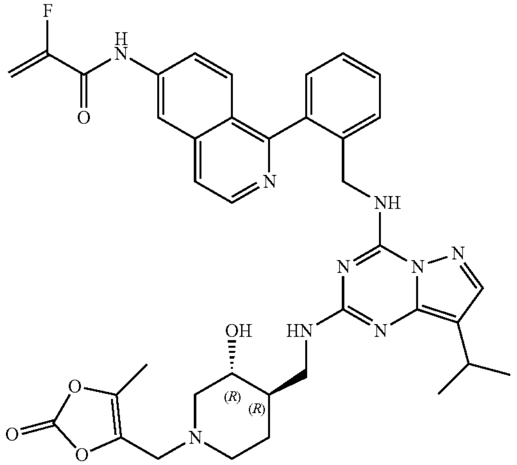 |

-continued
| No. | Compound |
|---|---|
| 9 | 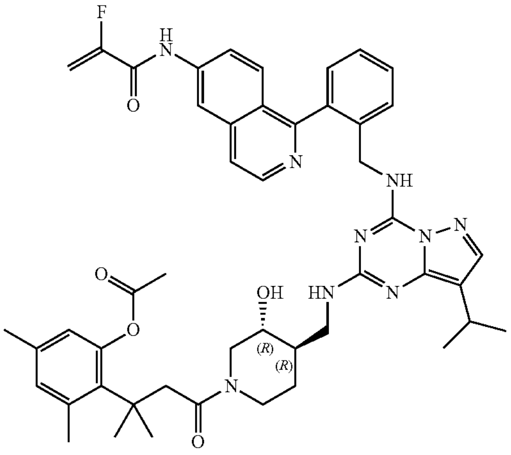 |
| 10 | 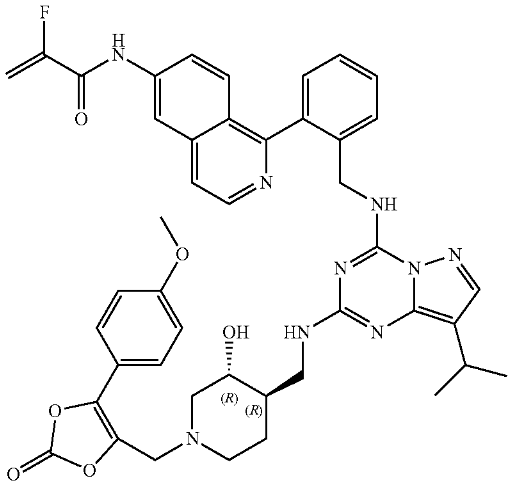 |
| 11 | 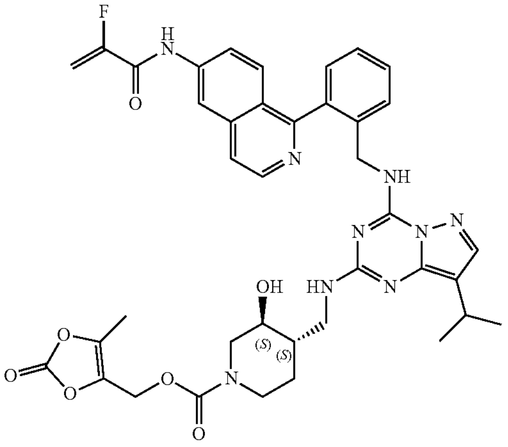 |
-continued
| No. | Compound |
|---|---|
| 12 | 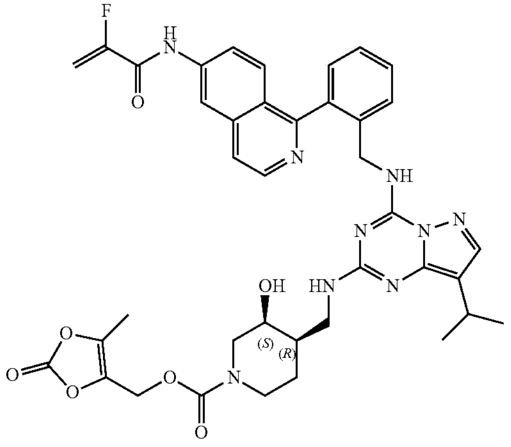 |
| 13 | 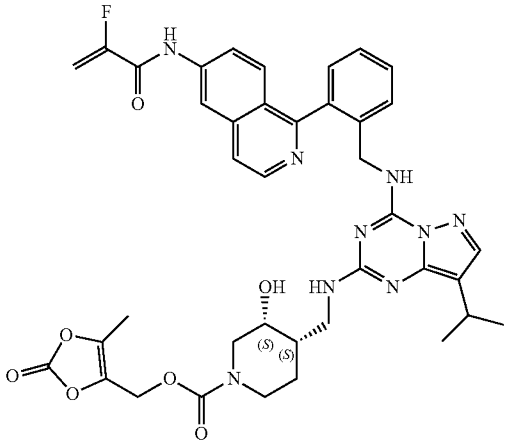 |
| 14 | 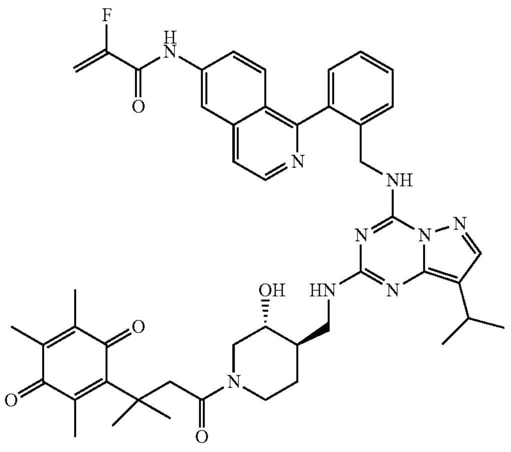 [SMILES: C=C(F)C(=O)Nc1ccc2c(-c3ccccc3CNc3nc(NC[C@H]4CCN(C(=O)CC(C)(C)C5=C(C)C(=O)C(C)=C(C)C5=O)C[C@@H]4O)nc4c(C(C)C)cnn34)nccc2c1] |

-continued
| No. | Compound |
| --- | --- |
| 15 | 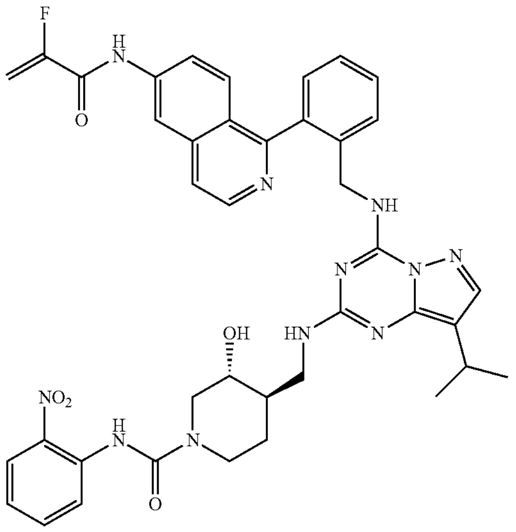 [SMILES: C=C(F)C(=O)Nc1ccc2c(-c3ccccc3CNc3nc(NC[C@H]4CCN(C(=O)Nc5ccccc5[N+](=O)[O-])C[C@@H]4O)nc4c(C(C)C)cnn34)nccc2c1] |
| 16 | 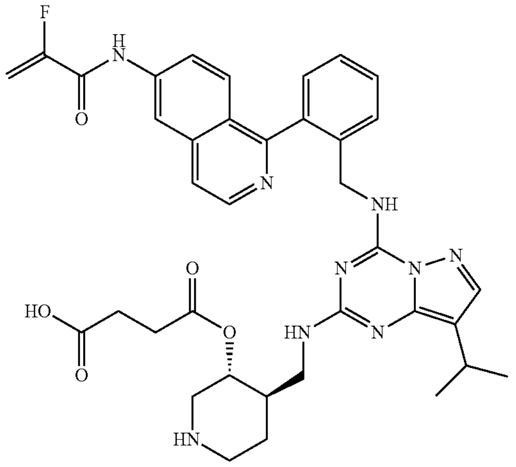 [SMILES: C=C(F)C(=O)Nc1ccc2c(-c3ccccc3CNc3nc(NC[C@H]4CCNC[C@@H]4OC(=O)CCC(=O)O)nc4c(C(C)C)cnn34)nccc2c1] |
| 17 | 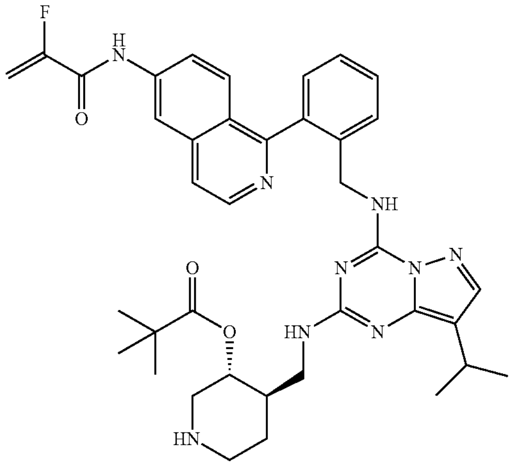 [SMILES: C=C(F)C(=O)Nc1ccc2c(-c3ccccc3CNc3nc(NC[C@H]4CCNC[C@@H]4OC(=O)C(C)(C)C)nc4c(C(C)C)cnn34)nccc2c1] |
-continued
| No. | Compound |
| --- | --- |
| 18 | 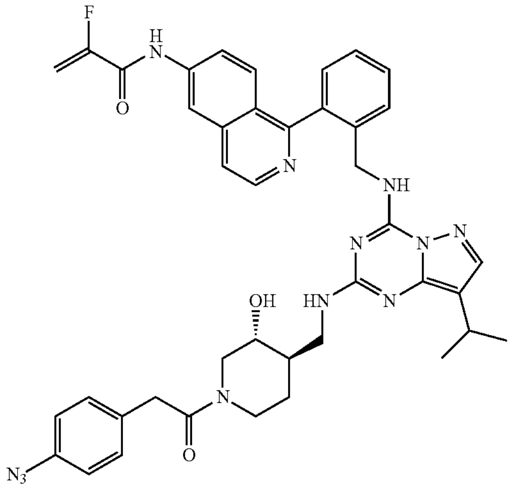 [SMILES: C=C(F)C(=O)Nc1ccc2c(-c3ccccc3CNc3nc(NC[C@H]4CCN(C(=O)Cc5ccc(N=[N+]=[N-])cc5)C[C@@H]4O)nc4c(C(C)C)cnn34)nccc2c1] |
| 19 | 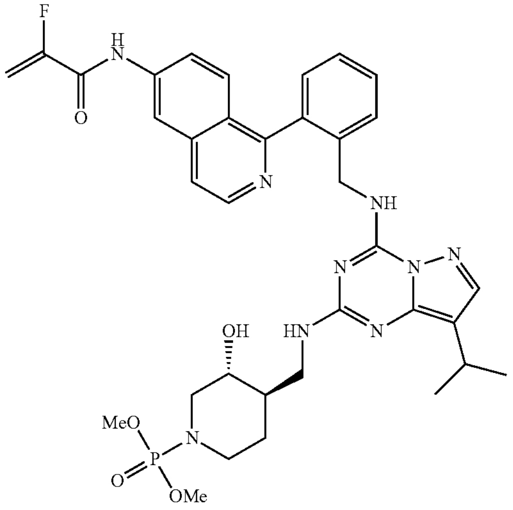 [SMILES: C=C(F)C(=O)Nc1ccc2c(-c3ccccc3CNc3nc(NC[C@H]4CCN(P(=O)(OC)OC)C[C@@H]4O)nc4c(C(C)C)cnn34)nccc2c1] |
| 20 | 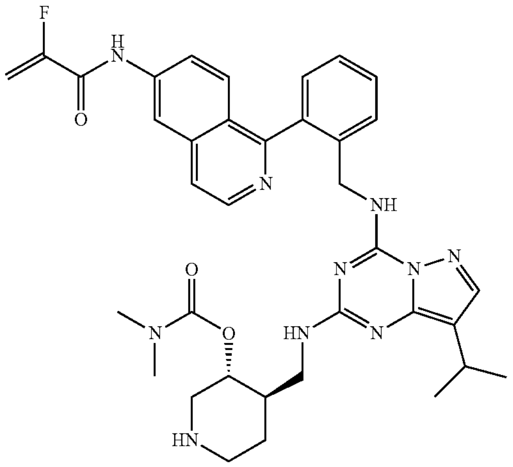 [SMILES: C=C(F)C(=O)Nc1ccc2c(-c3ccccc3CNc3nc(NC[C@H]4CCNC[C@@H]4OC(=O)N(C)C)nc4c(C(C)C)cnn34)nccc2c1] |
Wherein also this embodiment includes enantiomers, stereoisomeric forms, mixtures of enantiomers, diastereomers, mixtures of diastereomers, racemates of the above mentioned compounds or a pharmaceutically acceptable salt thereof.

Preferably, said compound is any one of the compounds 2, 3, 4, 5, 6, and 8, as defined above, wherein more preferably, said compound is any one of the compounds 2, 3, 4, 5 and 6, as defined above, and even more preferably is compound 3, as defined in the above table.

Also this particular embodiment includes enantiomers, stereoisomeric forms, mixtures of enantiomers, diastereomers, mixtures of diastereomers, racemates of the above mentioned compounds or pharmaceutically acceptable salts thereof.

In one embodiment of the compounds according to the present invention of formula I, if $R^1$ is aryl substituted with $—NO_2$ or $—N_3$, then $L^1$ is not $—CH_2—$ or $—CH(CH_3)—$.

In a further aspect the present invention relates to a pharmaceutical composition comprising a compound according to the present invention, as defined herein, together with at least one pharmaceutically acceptable carrier, excipient and/or diluent.

In one embodiment of such pharmaceutical composition, the pharmaceutical composition is formulated for oral administration. Preferably, such pharmaceutical composition is in a form selected from tablets, lozenges, pills, capsules, solutions, suspensions, emulsions and sprays.

The present invention also relates to compound or pharmaceutical composition according to the present invention, for use as a pharmaceutically active agent, wherein, preferably, said pharmaceutically active agent has an inhibitory activity on cyclin-dependent kinase 7 (cdk7).

The present invention also relates to compound or pharmaceutical composition according to the present invention, for use in a method of prevention and/or treatment of a disease which is associated with inhibition of apoptosis, abnormal transcriptional activity and/or cell cycle arrest by aberrant activity and/or overexpression of one or several cyclin-dependent kinases (CDKs), in particular of cyclin-dependent kinase 7 (CDK7), wherein the disease is preferably selected from proliferative diseases, infectious diseases including opportunistic diseases, immunological diseases, autoimmune diseases, and inflammatory diseases.

In one embodiment of such compound or pharmaceutical composition for use according to the present invention, the proliferative disease is a cancer, preferably a cancer selected from the group comprising or consisting of: adenocarcinoma, choroidal melanoma, acute leukemia, acoustic neurinoma, ampullary carcinoma, anal carcinoma, astrocytoma, basal cell carcinoma, pancreatic cancer, Desmoid tumor, bladder cancer, bronchial carcinoma, estrogen dependent and independent breast cancer, Burkitt's lymphoma, corpus cancer, Carcinoma unknown primary tumor (CUP-syndrome), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic tumor, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymphomas, stomach cancer, malignant melanoma, malignant neoplasia, malignant tumors gastrointestinal tract, breast carcinoma, rectal cancer, medulloblastomas, melanoma, meningiomas, Hodgkin's/Non-Hodgkin's lymphoma, mycosis fungoides, nasal cancer, neurinoma, neuroblastoma, kidney cancer, renal cell carcinomas, oligodendroglioma, esophageal carcinoma, osteolytic carcinom as and osteoplastic carcinomas, osteosarcomas, ovarian carcinoma, pancreatic carcinoma, penile cancer, plasmacytoma, prostate cancer, pharyngeal cancer, rectal carcinoma, retinoblastoma, vaginal cancer, thyroid carcinoma, esophageal cancer, T-cell lymphoma, thymoma, tube carcinoma, eye tumors, urethral cancer, urologic tumors, urothelial carcinoma, vulva cancer, wart appearance, soft tissue tumors, soft tissue sarcoma, Nephroblastoma, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypothalamic glioma, cerebellar astrocytoma, cerebral astrocytoma, neuroectodermal tumor, pineal tumors, sarcoma of the uterus, salivary gland cancers, anal gland adenocarcinomas, mast cell tumors, pelvis tumor, ureter tumor, hereditary papillary renal cancers, sporadic papillary renal cancers, intraocular melanoma, hepatocellular carcinoma, cholangiocarcinoma, mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-celllymphoma, lymphoma of the central nervous system, malignant fibrous histiocytoma, lymph sarcoma, rhabdomyosarcoma, malignant histiocytosis, fibroblastic sarcoma, hemangiosarcoma, hemangiopericytoma, leiomyosarcoma (LMS), canine mammary carcinoma, and feline mammary carcinoma.

In one embodiment of such compound or pharmaceutical composition for use according to the present invention, the infectious disease including opportunistic diseases is selected from the group comprising or consisting of AIDS, Adenovirus Infection, Alveolar Hydatid Disease (AHD), Amoebiasis, Angiostrongyliasis, Anisakiasis, Anthrax, Babesiosis, Balantidiasis, *Baylisascaris* Infection, *Bilharzia* (Schistosomiasis), *Blastocystis hominis* Infection, Lyme Borreliosis, Botulism, Brainerd Diarrhea, Brucellosis, Bovine Spongiform Encephalopathy (BSE), Candidiasis, Capillariasis, Chronic Fatigue Syndrome (CFS), Chagas Disease, Chickenpox, *Chlamydia pneumoniae* Infection, Cholera, Chronic Fatigue Syndrome, Creutzfeldt-Jakob Disease (CJD), Clonorchiasis, Cutaneous Larva migrans (CLM), Coccidioidomycosis, Conjunctivitis, Coxsackievirus A16 (Cox A16), Cryptococcal disease, Cryptosporidiosis, West Nile fever, Cyclosporiasis, Neurocysticercosis, Cytomegalovirus Infection, Dengue Fever, *Dipylidium caninum* Infection, Ebola Hemorrhagic Fever (EHF), Alveolar Echinococcosis (AE), Encephalitis, *Entamoeba coli* Infection, *Entamoeba dispar* Infection, *Entamoeba hartmanni* Infection, *Entamoeba polecki* Infection, Pinworm Infection, Enterovirus Infection (Polio/Non-Polio), Epstein Barr Virus Infection, *Escherichia coli* Infection, Foodborne Infection, Aphthae epizooticae, Fungal Dermatitis, Fungal Infections, Gastroenteritis, Group A streptococcal Disease, Group B streptococcal Disease, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis, Lassa Fever, Leishmaniasis, Visceral leishmaniasis (VL), Malaria, Marburg Hemorrhagic Fever, Measles, Meningitis, *Mycobacterium avium* Complex (MAC) Infection, *Naegleria* Infection, Nosocomial Infections, Nonpathogenic Intestinal Amebae Infection, Onchocerciasis, Opisthorchiasis, Papilloma virus Infection, Parvovirus Infection, Plague, *Pneumocystis* Pneumonia (PCP), Polyomavirus Infection, Q Fever, Rabies, Respiratory Syncytial Virus (RSV) Infection, Rheumatic Fever, Rift Valley Fever, Rotavirus Infection, Roundworms Infection, *Salmonellosis*, Scabies, Shigellosis, Shingles, Sleeping Sickness, Smallpox, Streptococcal Infection, Tapeworm Infection, Tetanus, Toxic Shock Syndrome, Tuberculosis, duodenum, *Vibrio parahaemolyticus* Infection, *Vibrio* septicemia, Viral Hemorrhagic Fever, Warts, Waterborne infectious Diseases, Varicella-Zoster Virus infection, Pertussis and Yellow Fever.

In one embodiment of such compound or pharmaceutical composition for use according to the present invention, the immunological disease and/or autoimmune disease is selected from the group comprising or consisting of: asthma, diabetes, rheumatic diseases, AIDS, rejection of transplanted organs and tissues, rhinitis, chronic obstructive pulmonary diseases, osteoporosis, ulcerative colitis, sinusitis, lupus erythematosus, recurrent infections, atopic dermatitis/eczema and occupational allergies, food allergies, drug allergies, severe anaphylactic reactions, anaphylaxis, manifestations of allergic diseases, primary immunodeficiencies, antibody deficiency states, cell mediated immunodeficiencies, severe combined immunodeficiency, DiGeorge syndrome, Hyper IgE syndrome (HIES), Wiskott-Aldrich syndrome (WAS), ataxia-telangiectasia, immune mediated cancers, white cell defects, autoimmune diseases, systemic lupus erythematosus (SLE), rheumatoid arthritis (RA), multiple sclerosis (MS), immune-mediated or Type 1 Diabetes Mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, Hashimoto's disease, dermatomyositis, Goodpasture syndrome (GPS), myasthenia gravis (MG), Sympathetic ophthalmia, Phakogene Uveitis, chronical aggressive hepatitis, primary biliary cirrhosis, autoimmune hemolytic anemia and Werlhof's disease.

In one embodiment of such compound or pharmaceutical composition for use according to the present invention, the inflammatory disease is caused, induced, initiated and/or enhanced by bacteria, viruses, prions, parasites, fungi, and/or is caused by irritative, traumatic, metabolic, allergic, autoimmune, or idiopathic agents.

In one embodiment of such compound or pharmaceutical composition for use according to the present invention, the inflammatory disease is selected from the group comprising or consisting of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, and inflammatory diseases of the larynx.

In one embodiment of such compound or pharmaceutical composition for use according to the present invention, the inflammatory disease is selected from inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx, wherein preferably said inflammatory diseases are selected from the group comprising abscessation, acanthamoeba infection, acne vulgaris, actinomycosis, acute inflammatory dermatoses, acute laryngeal infections of adults, acute multifocal placoid pigment epitheliopathy, acute (thermal) injury, acute retinal necrosis, acute suppurative otitis media, algal disorders, allergic contact dermatitis, amyloidosis angioedema, ankylosing spondylitis, aspergillosis, atopic dermatitis, pseudorabies, autoantibodies in vasculitis, bacterial disorders, bacterial laryngitis, bacterial meningitis, Behçet's disease (BD), birdshot choroidopathy, Gilchrist's disease, Borna disease, brucellosis, bullous myringitis, bursitis, candidiasis, canine distemper encephalomyelitis, canine distemper encephalomyelitis in immature animals, canine hemorrhagic fever, canine herpes virus encephalomyelitis, cholesteatoma, chronic granulomatous diseases (CGD), chronic inflammatory dermatoses, chronic relapsing encephalomyelitis, chronic suppurative otitis media, Ocular Cicatricial pemphigoid (OCP), common upper respiratory infection, granuloma, Crohn's disease, cryptococcal disease, dermatomyositis, diphtheria, discoid lupus erythematosus (DLE), drug-induced vasculitis, drug or hypersensitivity reaction, encephalitozoonosis, eosinophilic meningoencephalitis, Erythema multiforme (EM), feline leukemia virus, feline immunodeficiency virus, feline infectious peritonitis, feline Polioencephalitis, feline spongiform encephalopathy, fibromyalgia, Fuchs Heterochromic Uveitis, gastroesophageal (laryngopharyngeal) reflux disease, giant cell arteritis, glanders, glaucomatocyclitic crisis, gonorrhea granular myringitis, Granulomatous meningoencephalitis (GME), herpes simplex, histoplasmosis, idiopathic diseases, idiopathic inflammatory disorders, immune and idiopathic disorders, infections of the immunocompromised host, infectious canine hepatitis, inhalation laryngitis, interstitial nephritis, irritant contact dermatitis, juvenile rheumatoid arthritis, Kawasaki's disease, La Crosse virus encephalitis, laryngeal abscess, laryngotracheobronchitis, leishmaniasis, lens-induced uveitis, leprosy, leptospirosis, leukemia, lichen planus, lupus, lymphoma, meningitis, meningoencephalitis in greyhounds, miscellaneous meningitis/meningoencephalitis, microscopic polyangiitis, multifocal choroiditis, multifocal distemper encephalomyelitis in mature animals, multiple sclerosis, Muscle Tension Dysphonia (MTD), mycotic (fungal) diseases, mycotic diseases of the CNS, necrotizing encephalitis, neosporosis, old dog encephalitis, onchocerciasis, parasitic encephalomyelitis, parasitic infections, Pars planitis, parvovirus encephalitis, pediatric laryngitis, pollution and inhalant allergy, polymyositis, post-vaccinal canine distemper encephalitis, prion protein induced diseases, protothecosis, protozoal encephalitis-encephalomyelitis, psoriasis, psoriatic arthritis, pug dog encephalitis, radiation injury, radiation laryngitis, radionecrosis, relapsing polychondritis, Reiter's syndrome, retinitis pigmentosa, retinoblastoma, rheumatoid arthritis, Rickettsial disorders, rocky mountain spotted fever, salmon poisoning disease (SPD), Sarcocystosis, sarcoidosis, schistosomiasis, scleroderma, Rhinoscleroma, serpiginous choroiditis, shaker dog disease, Sjogren's syndrome, spasmodic croup, spirochetal (syphilis) diseases, spongiotic dermatitis, sporotrichosis, steroid responsive meningitis-arteritis, Stevens-Johnson syndrome (SJS, EM major), epiglottitis, sympathetic ophthalmia, Syngamosis, syphilis, systemic vasculitis in sarcoidosis, Takayasu's arteritis, tendinitis (tendonitis), Thromboangiitis obliterans (Buerger Disease), tick-borne encephalitis in dogs, toxic epidermal necrolysis (TEN), toxocariasis, toxoplasmosis, trauma, traumatic laryngitis, trichinosis, trypanosomiasis, tuberculosis, tularemia, ulcerative colitis, urticaria (hives), vasculitis, vasculitis and malignancy, vasculitis and rheumatoid arthritis, vasculitis in the idiopathic inflammatory myopathies, vasculitis of the central nervous system, vasculitis secondary to bacterial, fungal, and parasitic infection, viral disorders, viral laryngitis, vitiligo, vocal abuse, vocal-cord hemorrhage, Vogt-Koyanagi-Harada syndrome (VKH), Wegener's granulomatosis, and Whipple's disease.

The present invention also relates to the use of a compound as defined herein for the manufacture of a medicament for the prevention and/or treatment of a disease which is associated with inhibition of apoptosis, abnormal transcriptional activity and/or cell cycle arrest by aberrant activity and/or overexpression of one or several cyclin-dependent kinases (CDKs), in particular of cyclin-dependent kinase 7 (CDK7), wherein the disease is preferably selected from proliferative diseases, infectious diseases including opportunistic diseases, immunological diseases, autoimmune diseases, and inflammatory diseases, all of which are as defined herein.

The present invention also relates to a method of prevention and/or treatment of a disease which is associated with inhibition of apoptosis, abnormal transcriptional activity and/or cell cycle arrest by aberrant activity and/or overexpression of one or several cyclin-dependent kinases (CDKs), in particular of cyclin-dependent kinase 7 (CDK7), wherein the disease is preferably selected from proliferative diseases, infectious diseases including opportunistic diseases, immunological diseases, autoimmune diseases, and inflammatory diseases, all of which diseases are as defined herein, said method comprising the administration of a compound according to the present invention to a patient in need thereof.

In one embodiment, the patient in need thereof is a mammal. In one embodiment, the patient in need thereof is a human being. In another embodiment, the patient in need thereof is a non-human animal.

The compounds of the present invention are highly efficient inhibitors of CDK7 threonine/serine kinase and/or its complex, CDK7/MAT1/CycH. The inventive compounds are suitable for the use as a pharmaceutically active agent. The inventive compounds are suitable for the prevention and/or treatment of diseases associated with, accompanied by, caused by and/or induced by CDK7 and its complex, in particular a hyperfunction or dysfunction thereof. The inventive compounds are thus suitable for the prevention and/or treatment of CDK7-associated diseases or disorders and CDK7 complex induced disorders.

The inventive compounds are also useful in the manufacture of a medicament or of a pharmaceutical composition for the prevention and/or treatment of diseases associated with, accompanied by, caused by and/or induced by CDK7 and its complex, in particular a hyperfunction or dysfunction thereof. The inventive compounds are further used in the manufacture of a medicament or of a pharmaceutical composition for the prevention and/or treatment of diseases induced by CDK7 and/or its complex.

In one embodiment, such disease is selected from proliferative diseases, infectious diseases including opportunistic diseases, immunological diseases, autoimmune diseases, and inflammatory diseases, as defined herein.

Further advantageous features, aspects and details of the invention are evident from the dependent claims, the description, the examples and the drawings.

The term "substituted" as used herein is meant to indicate that a hydrogen atom where present and attached to a member atom within a group, or several such hydrogen atoms, may be replaced by a suitable group, including, but not limited to $C_1$-$C_3$ alkyl, —$NO_2$, —$N_3$, —OH, —(C═O)OH, $NH_2$, heterocycle, alkoxy, in particular $C_1$-$C_3$ alkoxy, halogen, such as fluorine or chlorine, $C_1$-$C_3$ haloalkyl, methylhydroxyl, COOMe, C(O)H, COOH, OMe, $OCF_3$, where such substituent is not otherwise specified.

The term "alkyl" refers to a monovalent straight, branched or cyclic chain, saturated aliphatic hydrocarbon radical having a number of carbon atoms in the specified range. Thus, for example, "$C_1$-$C_{11}$ alkyl" refers to any of the alkyl isomers having 11, 10, 9, 8, 7, 6, 5, 4, 3, 2 carbon atoms, or 1 carbon atom in their hydrocarbon chain. As a further example, "$C_1$-$C_6$ alkyl" refers to any of the hexyl alkyl and pentyl alkyl isomers as well as n-, iso-, sec-, and t-butyl, n- and isopropyl, cyclic propyl, ethyl and methyl. Likewise the term "$C_1$-$C_3$ alkyl" refers to any of the n- and isopropyl, cyclic propyl, ethyl and methyl radicals, any of which may be further substituted. An example of a methyl radical that is further substituted is a halomethyl, such as —$CH_2F$, $CHF_2$, or $CF_3$.

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl.

The term "aryl" refers to (i) optionally substituted 5- and 6-membered aromatic rings and (ii) optionally substituted 9- and 10-membered bicyclic, fused ring systems in which at least one ring is aromatic. Examples include, but are not limited to phenyl, tolyl, xylyl and naphthyl.

The term "phenyl" as used herein is meant to indicate an aromatic ring structure of formula —$C_6H_5$, and such term includes an optionally substituted or non-substituted phenyl group.

The term "benzyl" as used herein is meant to indicate a structure of formula —$CH_2$—$C_6H_5$, wherein such term includes an optionally substituted or non-substituted benzyl group.

The term "heterocyclyl" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to S(O) or $S(O)_2$. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the compounds of the invention, its active metabolites or isomers and salts according to the invention and their application can be performed according to known pharmaceutical methods.

While the compounds of the invention, useable according to the invention for use in therapy, may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention or pharmaceutical composition of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems.

In a preferred embodiment a medicament or pharmaceutical composition of the present invention is formulated and suitable for oral administration or for intraperitoneal administration.

Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms, in particular those formulated for oral administration include solids, and in particular tablets, filled capsules, powder and pellet forms, and liquids, in particular aqueous or non-aqueous solutions, preferably aqueous solutions, suspensions, emulsions, elixirs, and capsules filled with the same, all for oral use.

Other suitable forms for administration may be suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or an enantiomer, stereoisomeric form, mixture of enantiomers, diastereomer, mixture of diastereomer, racemate or a pharmaceutically acceptable salt thereof of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, aqueous solutions, suspensions or emulsions may be useful for oral administration. Parenteral injection liquid preparations can be formulated as solutions in aqueous solution, e.g. aqueous polyethylene glycol solution.

The chemical compounds according to the present invention may thus also be formulated for parenteral administration (e.g. by injection, for example bolus injection or continuous infusion) and may be presented in unit dose form in ampoules, pre-filled syringes, small volume infusion or in multi-dose containers with an added preservative. They may also be formulated for oral administration, either in solid or liquid form. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

For administration, the compounds of the present invention may, in one embodiment, be administered in a formulation containing 0,001% to 70% per weight of the compound, preferably between 0.01% to 70% per weight of the compound, even more preferred between 0.1% and 70% per weight of the compound. In one embodiment, a suitable amount of compound administered is in the range of from 0.01 mg/kg body weight to 1 g/kg body weight.

Compositions suitable for administration also include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

The present inventors have surprisingly identified compounds that show an inhibitory effect on cyclin-dependent kinases, in particular cyclin-dependent kinase 7 (CDK7), but that result in a much higher bioavailability of their active form, when administered to a patient, in particularly when administered orally. Without wishing to be bound by any theory, the present inventors believe that the compounds according to the present invention, upon administration, in particular oral administration, get converted into their active form within the metabolism of the patient and thus increase the bioavailability of such active form. Accordingly, the compounds according to the present invention, upon administration, cause a higher exposure level in plasma, as measured in terms of their pharmacokinetic profile in comparison to a direct administration of the active form. They also show a remarkable inhibitory effect on tumor growth.

The term "active form" as used herein, is meant to refer to the compound having the formula This is compound 64, as disclosed in WO2019/197546. The present inventors have surprisingly found that such compound, when administered orally, has a relatively low bioavailiability, in that it does not reach the intended site of action for unknown reasons. The resultant pharmacokinetic parameters (in particular $C_{max}$, and AUC) are relatively low. In contrast thereto, if a compound according to the present invention is administered, the inventors have found that the compound(s) according to the present invention is(are) converted into compound 64, likely by a hydrolytic mechanism, and the corresponding pharmacokinetic parameters for compound 64 then are dramatically higher, typically by a factor of several orders of magnitude (see also further below for details).

Moreover, the compounds according to the present invention are expected to show a much better efficacy in terms of their capacity to inhibit tumor growth, in comparison to a direct oral administration of compound 64 of WO2019/197546.

BRIEF DESCRIPTION OF THE TABLES AND FIGURES

Reference is now made to the figures and tables, wherein

Table 1 shows comparison quantitative data of selected compounds of present invention vs. active form (=cpd. 64 of WO2019/197546) in terms of in-vivo Pharmacokinetic profile by oral administration in CD-1 mice (male, BK/Lingchang/Vital River Laboratory Animal Co., Ltd.)

Table 2 Summarizes compounds 1-20 in terms of their structures and corresponding characteristics.

FIG. 1 shows the in-vivo efficacy data of selected compounds according to the present invention in the A2780 CDX model.

The invention is now further described by reference to the following examples which are intended to illustrate, not to limit the scope of the invention.

EXAMPLES

Example 1: In-Vivo Pharmacokinetic Study in CD-1 Mice_(Male, BK/Lingchang/Vital River Laboratory Animal Co., Ltd.)

Study Protocol

Pharmacokinetic (PK) study of compound 2, 3, 4, 5 and 6 of the present application, as well as for the compound 64 of WO2019/197546 (="active form") was conducted in CD-1 mice following administration of each compound. Compounds were prepared in 40% polyethylene glycol 400 in purified water (v/v %)(i.e. PEG400:water=40%:60% (v/v) and dosed orally at a dose of 40 and 100 mg/kg.

Data Analysis

Blood samples for bioanalysis were collected from saphenous vein at each time point (up to 24 hours). Plasma samples were analyzed by liquid chromatography-tandem mass spectrometry (LC-MS/MS). Plasma PK parameters ($C_{max}$, $T_{max}$, $T_{1/2}$, $T_{last}$, $AUC_{(0-t)}$ and % F) for the "active form" were estimated from noncompartmental analysis using WInnonlin (Pharsight).

The data obtained are shown in table 1 below ("PO1" and "PO2" in the table mean oral administration at a first and second concentration) and make it clear that an administration of the compounds according to the present invention results in much better pharmacokinetic parameters of the "active form", in comparison to a direct administration of the "active form".

Example 2: In Vivo A2780 Efficacy Study

A2780 (ECACC-93112519) human ovarian adenocarcinoma cells were suspended at $2\times10^6$ in 0.2 mL of phosphate-buffered saline (PBS) mixed with Matrigel (50:50). The prepared suspension was subcutaneously inoculated to each 6 to 8 weeks old female Balb/c nude mouse (Shanghai SIPPR/BK Laboratory Animal Co., LTD). 10 days after cell inoculation, when the average tumor size had reached 104 $mm^3$, the animals were randomized into 8 mice per group. The compounds of the present invention (or vehicle) were administered at the indicated concentrations of FIG. 1, once a day (QD) or twice a day (BID) from 10 days after tumor cell inoculation (Day 0). The administration was continued until the tumor size of vehicle groups reached over 2,000 $mm^3$ (10 days post $1^{st}$ administration). The tumor volume ($mm^3$) was calculated using formula $V=0.5\ a\times b$ where a and b are the long and short diameters of the tumor in mm. Tumor growth inhibition index (TGI) was calculated for each group using the formula: $TGI\ (\%)=[1-(Ti-T0)/(Vi-V0)]\times100$; Ti is the average tumor volume of the treatment group on the given day, To is the average tumor volume of the treatment group on the day when the treatment was started, Vi is the average tumor volume of the vehicle control group on the same day with Ti, and V0 is the average tumor volume of the vehicle group on the day of treatment start. Statistical analysis of difference in tumor volume among the groups was conducted on the data obtained on 8 days after administration. All data was analyzed using Graphpad Prism. $p<0.05$ is considered to be statistically significant.

The data are shown in FIG. 1 and demonstrate the capability of the compounds according to the present invention to reduce tumor growth considerably in comparison to the vehicle treated group.

Example 3: Derivatization of the General Scaffold

The presented compounds underwent derivatization according to the methods outlined below (Schemes 1-13). Resulting derivatives were examined for in-vivo Pharmacokinetic (PK) and in vivo A2780 efficacy using the assays described above (Example 1-2) and the results are summarized in Table 1 and FIG. 1. The synthesized compounds 1-20 are shown in Table 2.

Scheme 1: General Synthetic route
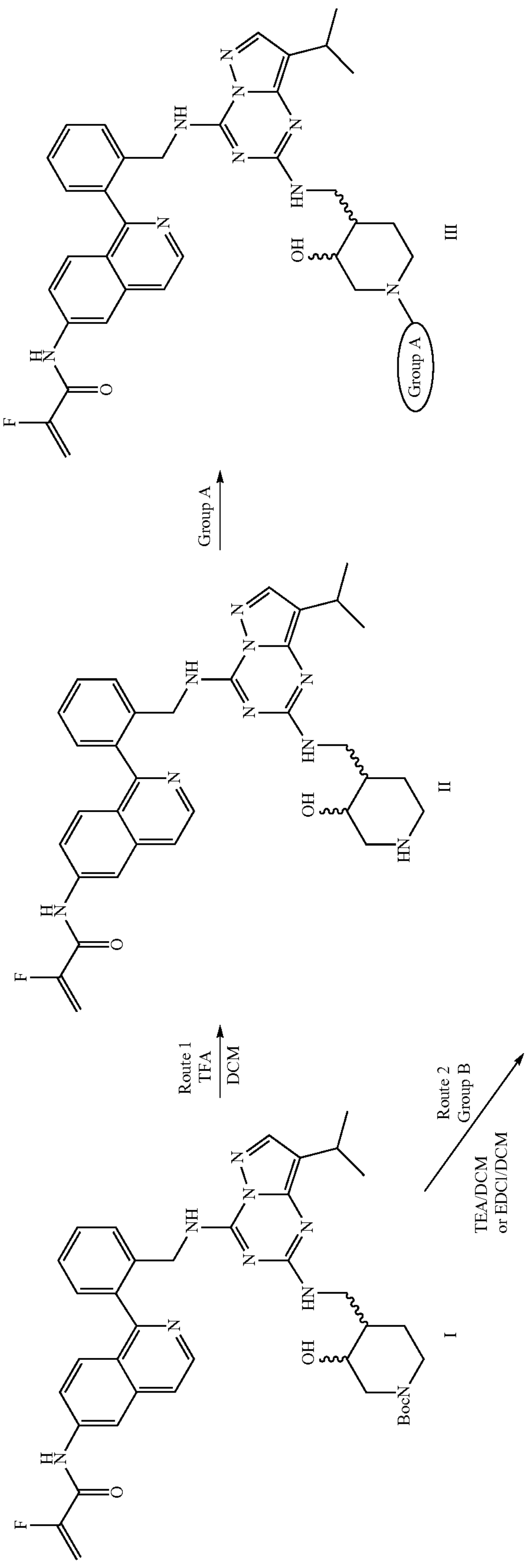
I
II
III

-continued
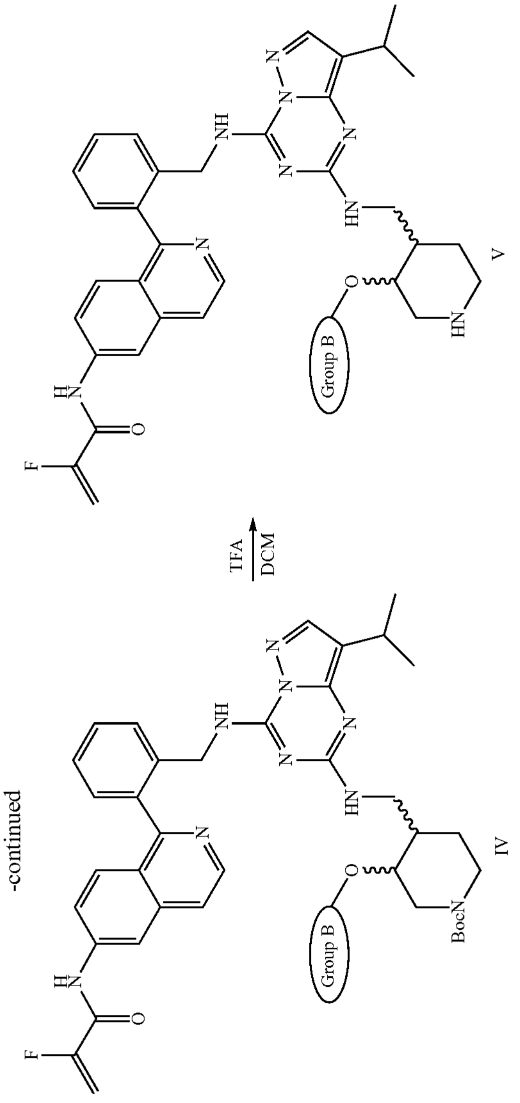
IV
V

The method to prepare compounds of formula III and V were shown in Scheme 1.

Synthetic procedure of compound I is published in WO2019197546A1.

Route 1: Compounds I can be treated with trifluoroacetic acid (TFA) to obtain the compounds of formula II. Compounds II can be treated with Group A in presence of base triphosgene, or 1-Ethyl-3-(3-dimethylaminopropyl)carbodiimide (EDCI) to obtain the compounds of formula III.

Route 2: Compounds I can be treated with Group B in presence of trimethylamine (TEA) or EDCI to obtain the compounds of formula IV. Compounds IV can be treated with TFA to obtain the compounds of formula V.

Commercial available below reagents were used for current invention.

tert-butyl (3S,4R)-4-(aminomethyl)-3-hydroxypiperidine-1-carboxylate, tert-butyl (3R,4R)-4-(aminomethyl)-3-hydroxypiperidine-1-carboxylate, tert-butyl (3S,4S)-4-(aminomethyl)-3-hydroxypiperidine-1-carboxylate and tert-butyl (3R,4S)-4-(aminomethyl)-3-hydroxypiperidine-1-carboxylate.

Group A: 4-(chloromethyl)-5-methyl-1,3-dioxol-2-one, 2-(4-azidophenyl)acetic acid, dimethyl phosphorochloridate and 4-(bromomethyl)-5-(4-methoxyphenyl)-1,3-dioxol-2-one Group B: acetic anhydride, succinic acid, pivalic acid, dimethylcarbamic acid and (2S)-2-(tert-butoxycarbonylamino)-3-methyl-butanoic acid.

General Schemes of Group A

Scheme 2: Synthetic route for A2

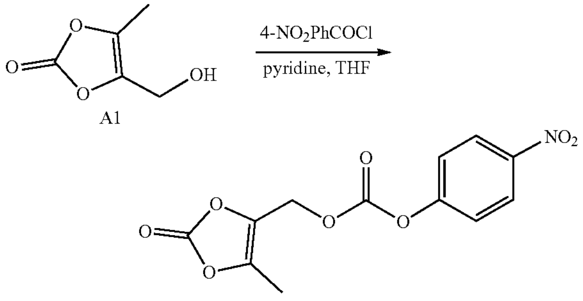

A1

A2

Procedure for Synthesis of A2

To a solution of A1 (14.5 g, 111.4 mmol, 1 eq) and pyridine (10.58 g, 133.7 mmol, 1.2 eq) in THF (200 mL) was added 4-nitrophenyl chloroformate (24.71 g, 122.6 mmol, 1.1 eq) in portions under ice-bath 0~5° C. The resultant solution was stirred at rt. for 15 hours to give pale yellow mixture. The mixture was concentrated in vacuum. The residue was diluted with EtOAc (800 mL), then, washed with water and brine. The organic layer was then dried over $Na_2SO_4$, concentrated in vacuum to give pale yellow solid. The crude solid was triturated with to give A2 (13 g, 44.04 mmol, 39.51% yield) as off-white solid.

Scheme 3: Synthetic route for A5, A6 and A7

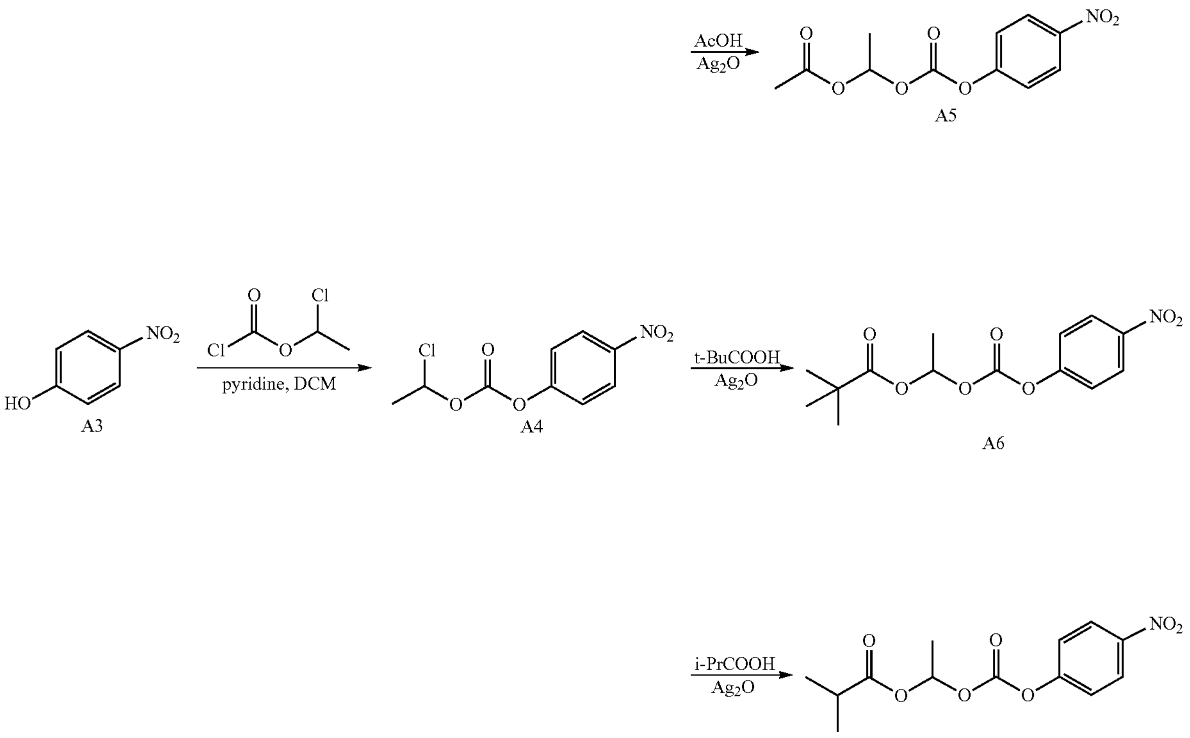

A5

A3

A4

A6

A7

Procedure for Synthesis of A4

To an ice cold reaction mixture containing A3 (500 mg, 3.59 mmol, 1 eq) and pyridine (284.31 mg, 3.59 mmol, 1. eq) in DCM (15 mL) was added 1-chloroethyl carbonochloridate (565.26 mg, 3.95 mmol, 1.1 eq). The mixture was stirred at 0° C. for 30 min and then at 15° C. for 1 hour to give a yellow mixture. LCMS showed the new spot was observed. The mixture was concentrated under reduced pressure to give residue. The residue was partitioned between EtOAc and $H_2O$. The aqueous phase was extracted with EtOAc. The combined organic extract was dried over anhydrous $Na_2SO_4$, filtered and concentrated under reduced pressure to give A4 (810 mg, 3.30 mmol, 91.7% yield) as white solid.

Procedure for Synthesis of A5

To a mixture of A4 (160 mg, 0.651 mmol, 1 eq) in AcOH (1.17 g, 19.54 mmol, 30 eq) was added $Ag_2O$ (150.96 mg, 0.651 mmol, 1 eq), the mixture was stirred at 95° C. for 2 hours to give a yellow mixture. TLC showed the new spot was observed. The mixture was partitioned between EtOAc and $H_2O$. The aqueous phase was extracted with EtOAc. The combined organic extract was dried over anhydrous $Na_2SO_4$, filtered and concentrated under reduced pressure to give A5 (110 mg, 0.408 mmol, 62.7% yield) as yellow oil.

Procedure for Synthesis of A6

To a solution of A4 (4 g, 16.29 mmol, 1 eq) in pivalic acid (33.27 g, 325.71 mmol, 20 eq) was added $Ag_2O$ (3.77 g, 16.29 mmol, 1 eq). The mixture was stirred at 95° C. for 2 hours to give a yellow mixture. TLC indicated the reaction was completed. The mixture was partitioned between EtOAc and $H_2O$. The aqueous phase was extracted with EtOAc. The combined organic layer was dried over anhydrous $Na_2SO_4$, filtered and concentrated under reduced pressure to give A6 (4.9 g, 15.74 mmol, 96.6% yield) as yellow oil.

Procedure for Synthesis of A7

To a mixture of A4 (4 g, 16.29 mmol, 1 eq) in 2-methylpropanoic acid (28.70 g, 325.80 mmol, 20 eq) was added $Ag_2O$ (3.77 g, 16.29 mmol, 1 eq), the mixture was stirred at 95° C. for 2 hours to give a yellow mixture. TLC showed the new spot was observed. The mixture was partitioned between EtOAc and $H_2O$. The organic layer was washed with aq. $NaHCO_3$. The combined organic layer was dried over anhydrous $Na_2SO_4$, filtered and concentrated under reduced pressure to give A7 (4.86 g, crude) as light yellow solid.

Scheme 4: Synthetic route for A7

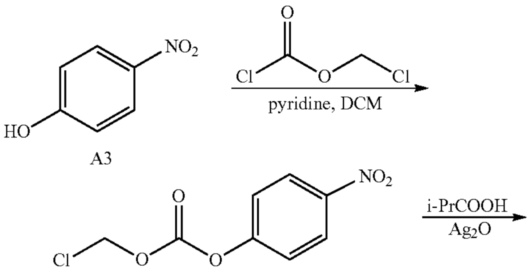

A3

A8

-continued

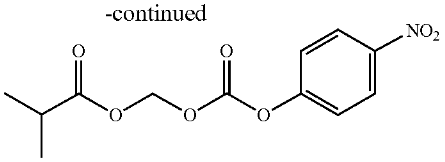

A9

Procedure for Synthesis of A8

To an ice cold reaction mixture containing A3 (5 g, 35.94 mmol, 1 eq) and pyridine (3.13 g, 39.54 mmol, 1.1 eq) in DCM was added chloromethyl carbonochloridate (5.10 g, 39.54 mmol, 1.1 eq). The mixture was stirred at ° C. for 30 min and then at 15° C. for 1 hour to give a yellow mixture. TLC showed the reactant was consumed. The mixture was concentrated under reduced pressure to give residue. The residue was partitioned between EtOAc and $H_2O$. The aqueous phase was extracted with EtOAc. The combined organic extract was dried over anhydrous $Na_2SO_4$, filtered and concentrated under reduced pressure to give A8 (7.2 g, 86.5% yield) as off-white solid.

Procedure for Synthesis of A9

To a mixture of A8 (7.2 g, 31.09 mmol, 1 eq) in isobutyric acid (54.78 g, 621.79 mmol, 20 eq) was added $Ag_2O$ (7.20 g, 31.09 mmol, 1 eq), the mixture was stirred at 95° C. for 2 hours to give a yellow mixture. TLC showed the new spot was observed. The mixture was partitioned between EtOAc and $H_2O$. The aqueous phase was extracted with EtOAc. The combined organic extract was dried over anhydrous $Na_2SO4$, filtered and concentrated under reduced pressure to give crude product. The crude product was purified by combi flash to give A9 (1.02 g, 3.60 mmol, 11.5% yield) as a yellow oil.

Scheme 5: Synthetic route for A17

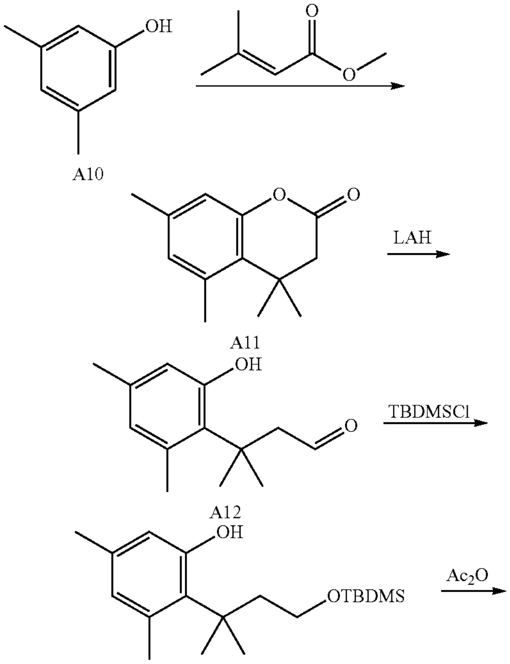

A10

A11

A12

A13

-continued

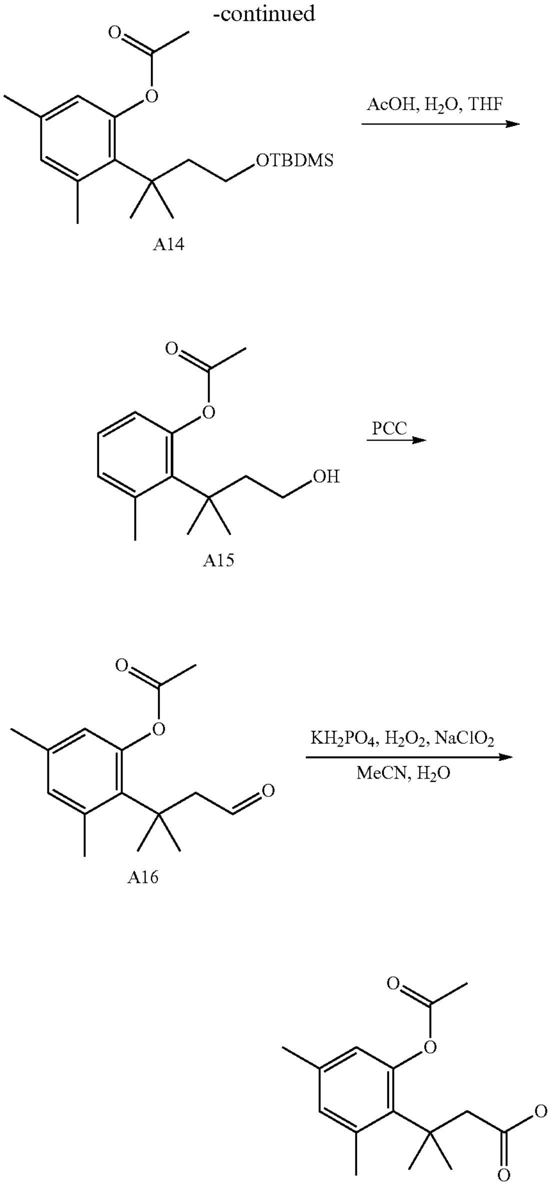

A14

A15

A16

A17

Procedure for Synthesis of A11

A10 (2 g, 16.37 mmol, 1 eq) and methyl 3-methylbut-2-enoate (2.06 g, 18.01 mmol, 1.1 eq) was added to methanesulfonic acid (2 mL) at 20° C., the mixture was heated to 70° C. and stirred for 17 hours to give a brown mixture. LCMS indicated the reaction was completed. The reaction mixture diluted with water and extracted with EtOAc. The combined organic layers were washed with brine, dried over $Na_2SO_4$, filtered and concentrated under reduced pressure to give crude product. The residue was purified by flash column chromatography to give (3.26 g, 15.96 mmol, 97.5% yield) of A11 as white solid.

Procedure for Synthesis of A12

To a solution of A11 (1.2 g, 5.87 mmol, 1 eq) in THF (18 mL) was added dropwise $LiAlH_4$ (234.12 mg, 6.17 mmol, 1.05 eq) in THF (25 mL) at 0° C. for 30 min. After addition, the mixture was stirred at 20° C. for 1 hour to give white suspension. LCMS indicated the reaction was completed. The mixture solution was quenched by water and 2N NaOH solution was added, then added water, dried over $Na_2SO_4$, filtered and concentrated under reduced pressure to give crude product. The residue was purified by flash column chromatography to give (800 mg, 3.84 mmol, 65.3% yield) of A12 as white solid.

Procedure for Synthesis of A13

A mixture of A12 (800 mg, 3.84 mmol, 1 eq), tert-Butyldimethylsilyl chloride (TBDMSCl, 694.65 mg, 4.61 mmol, 1.2 eq), imidazole (653.66 mg, 9.60 mmol, 2.5 eq) in DMF (8 mL) was degassed and purged with $N_2$ gas for 3 times, and then the mixture was stirred at 20° C. for 2 hours under $N_2$ atmosphere to give a colorless mixture. TLC indicated the reaction was completed. The reaction mixture diluted with water and extracted with EtOAc. The combined organic layers were washed with brine, dried over $Na_2SO_4$, filtered and concentrated under reduced pressure to (1.2 g, 3.72 mmol, 96.8% yield) of A13 as white solid.

Procedure for Synthesis of A14

To a solution of A13 (1.2 g, 3.72 mmol, 3.00 mL, 1 eq) in DCM (10 mL) was added TEA (752.91 mg, 7.44 mmol, 2 eq), 4-(Dimethylamino)pyridine (DMAP, 45.45 mg, 372.03 umol, 0.1 eq) and acetic anhydride (569.69 mg, 5.58 mmol, 1.5 eq) was dropwised at 0-5° C., the mixture was stirred at 20° C. for 16 hr to give a yellow mixture. TLC and LCMS indicated the reaction was completed. The mixture was diluted with water, extracted with EtOAc. The combined organic extract was washed with aq. $NaHCO_3$ and brine, dried over $Na_2SO_4$, filtered, concentrated under reduced pressure to give crude product. The residue was purified by flash column to give (1.02 g, 2.80 mmol, 75.2% yield) of A14 as colorless oil.

Procedure for Synthesis of A15

To a solution of A14 (500 mg, 1.37 mmol, 1 eq) in THE (1.25 mL) and water (1.25 mL) was added AcOH (3.94 g, 65.57 mmol, 47.81 eq) at ° C. The mixture was stirred at 20° C. for 16 hours to give a yellow mixture. LCMS indicated the reaction was completed. The reaction mixture was diluted with water and extracted with DCM. The pH was adjusted to around 8 by progressively adding aqueous $NaHCO_3$. The combined organic layers were washed with brine, dried over $Na_2SO_4$, filtered and concentrated under reduced pressure to give crude product. The residue was purified by flash column chromatography to give (300 mg, 1.20 mmol, 87.3% yield) of A15 as colorless oil.

Procedure for Synthesis of A16

To a solution of A15 (110 mg, 0.439 mmol, 1 eq) in DCM (3 mL) was added Pyridinium chlorochromate (PCC, 208.3 mg, 0.966 umol, 2.2 eq) at ° C. The mixture was stirred at 20° C. for 1 hour to give a yellow suspension. LCMS indicated the reaction was completed. The reaction mixture was concentrated under reduced pressure to give a residue. The residue was purified by flash column chromatography to give (103 mg, 0.414 mmol, 94.4% yield) of A16 as colorless oil.

Procedure for Synthesis of A17

To a solution of A16 (103 mg, 0.414 mmol, 1 eq) in MeCN (2.5 mL), a solution of $KH_2PO_4$ (112.90 mg, 0.829 mmol, 2 eq) in $H_2O$ (1 mL) and $H_2O_2$ (0.829 mmol, 79.71 uL, 30% purity, 2 eq) were added at 0° C. Then a solution of sodium chlorite (155.69 mg, 1.72 mmol, 4.15 eq) in $H_2O$ (2 mL) was added and the resulting mixture was stirred for 2 hours at 20° C. to give a yellow mixture. LCMS indicated the reaction was completed. The reaction mixture was quenched by addition $NaHSO_3$, and then diluted with water and extracted with DCM. The combined organic layers were washed with brine, dried over $Na_2SO_4$, filtered and concentrated under reduced pressure to give (98 mg, 0.37 mmol, 89.39% yield) of A17 as white solid.

Scheme 6: Synthetic route for A21

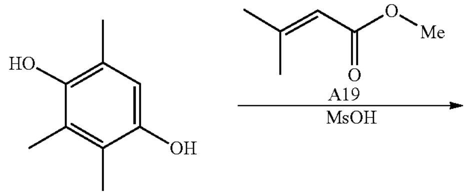

A18

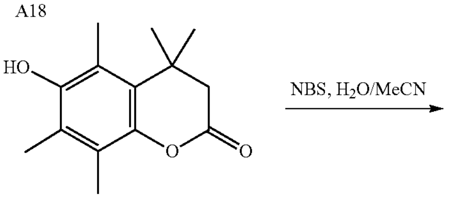

A20

-continued

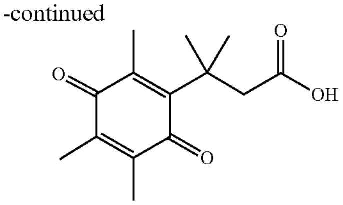

A21

Procedure for Synthesis of A20

A18 (500 mg, 3.29 mmol, 1 eq) and A19 (412.50 mg, 3.61 mmol, 441.17 uL, 1.1 eq) was added to MsOH (1 mL) at 20° C. The mixture was heated to 70° C. and stirred for 16 hr to give a brown mixture. The reaction mixture diluted with water (1 mL) and extracted with EtOAc (10 mL*3). The combined organic layers were washed with brine (10 mL), dried over Na2SO4, filtered and concentrated under reduced pressure to give a residue. The residue was purified by column chromatography to give A20 (355 mg, 1.52 mmol, 46.12% yield) as yellow solid.

Procedure for Synthesis of A21

A20 (352 mg, 1.50 mmol, 1 eq) and NBS (267.40 mg, 1.50 mmol, 1 eq) were added to a flask containing a mixture of CH3CN (4 mL) and H2O (1 mL) and kept under stirring at 20° C. for 30 mins. The solvent was evaporated under reduced pressure. The residue was recrystallized from CH2Cl2 and AcOEt (8:1, v/v) to give A21 (139 mg, 555.36 umol, 36.96% yield) as a brown solid.

General Schemes of Route 1

Scheme 7: Synthetic route for Compound 3

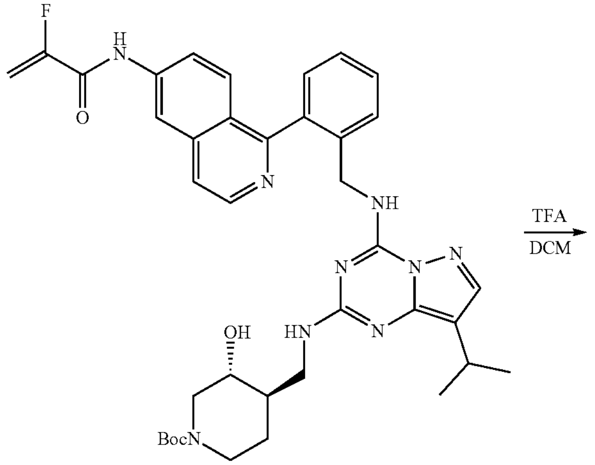

B1

-continued

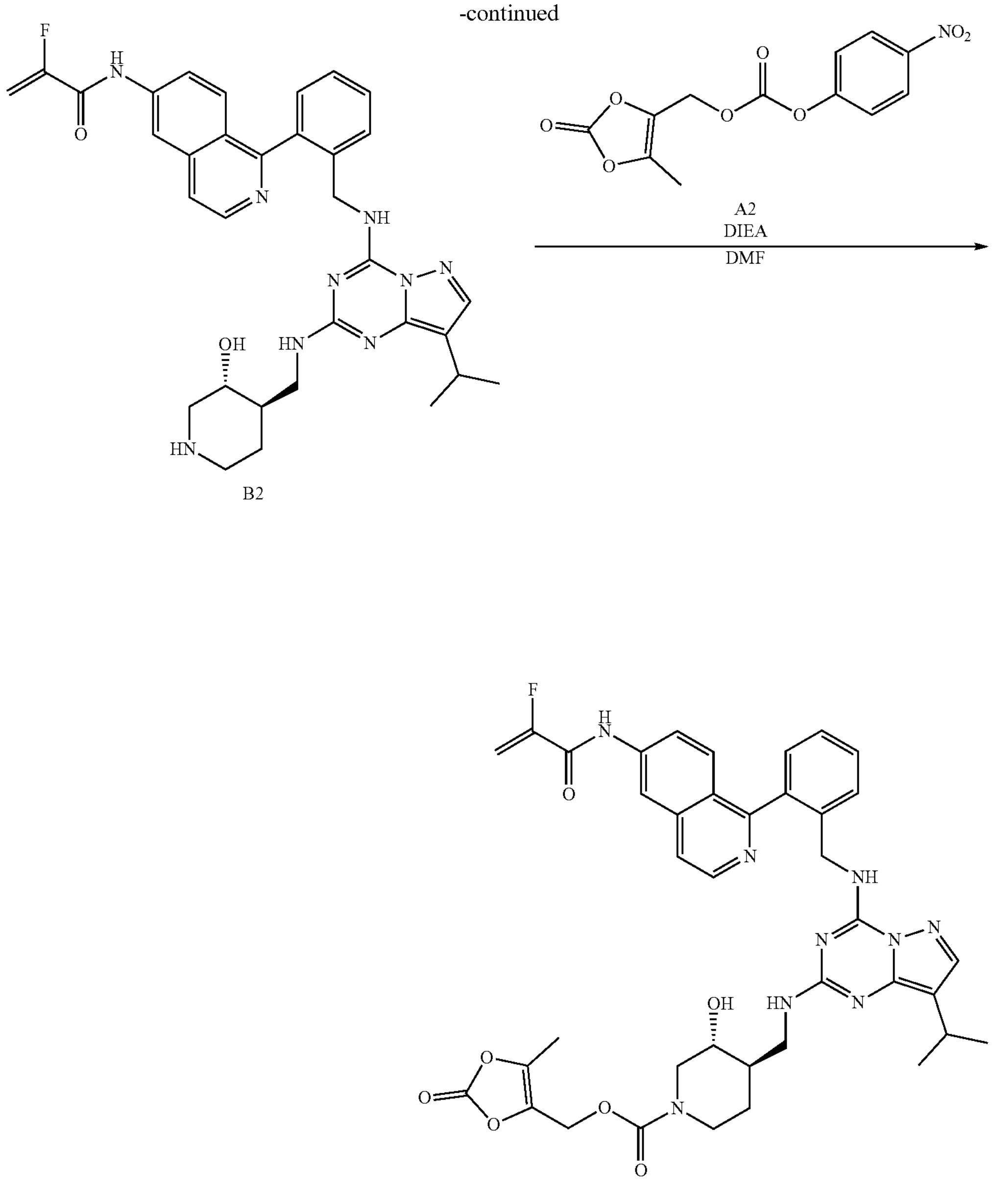

B2

Compound 3

Procedure for Synthesis of B2

To a solution of B1 (2 g, 2.82 mmol, 1 eq) in DCM (20 mL) was added TFA (6.16 g, 54.03 mmol, 19.17 eq) at 0° C., then, stirred at 0° C. for 3 hours to give pale yellow solution. The reaction was concentrated in vacuum at rt. The residue was dissolved with water (15 mL), washed with MTBE. The aqueous layer was added slowly into a pre-cooled (0° C.) suspension of DCM, THF and 2M $Na_2CO_3$ with stirring. The DCM layer was collected. The aqueous layer was extracted with DCM/THF=10/1. The combined DCM/THF layers were cooled to 0~5° C., treated with 4M HCl/MeOH (2.8 mL, 4 eq) slowly. The resulting mixture was concentrated in vacuum at 30° C. to give yellow gum. The gum was dissolved with water (30 mL), lyophilized to give B2 (1.46 g, 2.03 mmol, 71.9% yield) as pale yellow solid.

Procedure for Synthesis of Compound 3

To a solution of B2 (20 g, 27.81 mmol, 1 eq) and A2 (11.49 g, 38.94 mmol, 1.4 eq) in DMF (200 mL) was added DIEA (19.64 g, 151.98 mmol, 5.46 eq) at 0° C. The reaction was allowed to warm to 25° C. and stirred for 1 hour to give pale yellow solution. LCMS showed the reaction was completed. The solution was diluted with EA, washed with water and brine. The organic layer was dried over $Na_2SO_4$ and concentrated in vacuum to give pale yellow solid. The solid was purified by flash column. The product was lyophilized to give compound 3 (15.23 g, 19.88 mmol, 71.5% yield) as off-white solid.

Scheme 8: Synthetic route for Compound 8

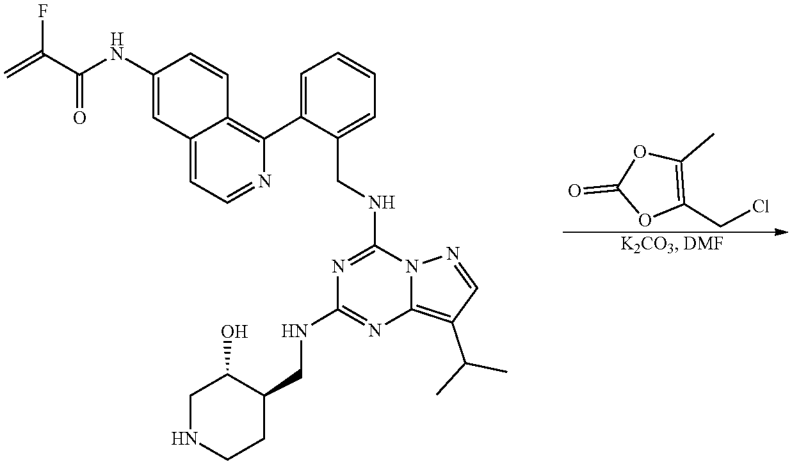

B2

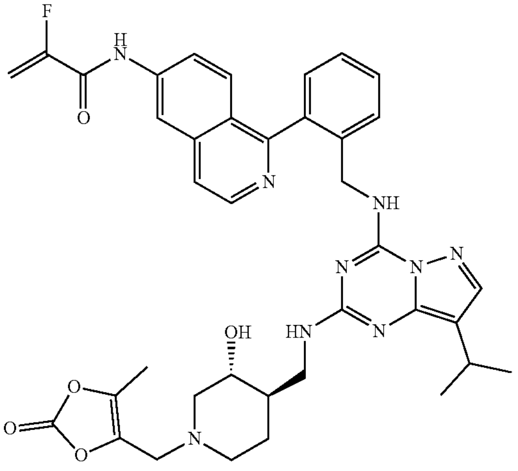

Compound 8

Procedure for Synthesis of Compound 8

A mixture of B2 (500 mg, 0.695 mmol, 1 eq) and $K_2CO_3$ (384.41 mg, 2.78 mmol, 4 eq) in DMF (5 mL) was stirred at 0° C. for 10 min. Then, 4-(chloromethyl)-5-methyl-1,3-dioxol-2-one (154.93 mg, 1.04 mmol, 1.5 eq) in DMF (1 mL) was added drop-wise at 0° C. and the reaction was allowed to warm to 20° C. and stirred for further 6 hours to give pale brown mixture. The mixture was diluted with EtOAc, washed with water and brine. The organic layer was dried over $Na_2SO_4$, concentrated in vacuum to give pale yellow solid. The solid was purified by flash column to give crude product and it was purified by prep-TLC to give Compound 8 (102.2 mg, 0.137 mmol, 19.8% yield) as off-white solid.

Scheme 9: Synthetic route for Compound 2

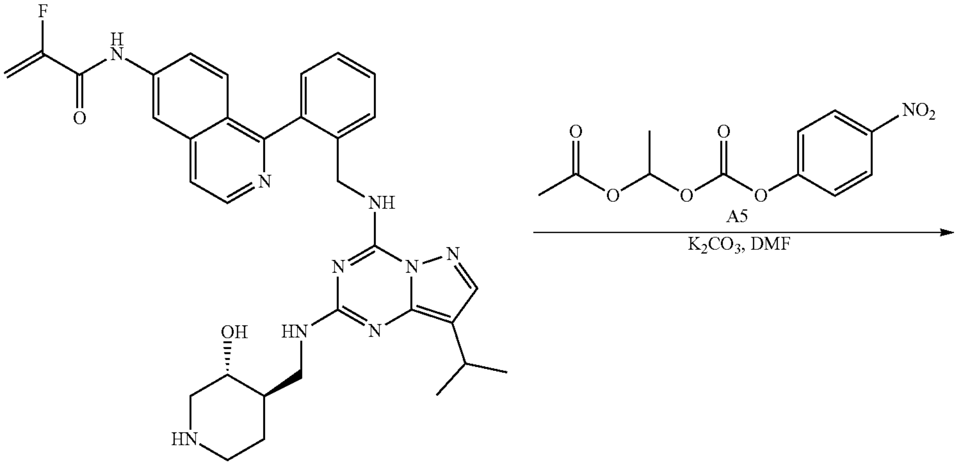

B2

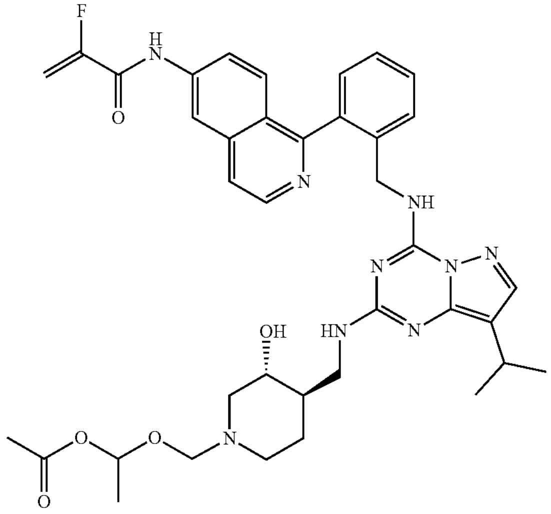

Compound 2

Procedure for Synthesis of Compound 2

To an ice cold reaction mixture containing B2 (100 mg, 0.164 mmol, 1 eq) and TEA (24.9 mg, 0.246 mmol, 1.5 eq) in DMF (2 mL) was added-A5 (4415 mg, 0.164 mmol, 1 eq). The mixture was stirred at 40° C. for 1 hour to give a yellow mixture. LCMS showed the new spot was observed. The mixture was concentrated under reduced pressure to give residue. The residue was partitioned between EtOAc and $H_2O$. The aqueous phase was extracted with EtOAc. The combined organic extract was dried over anhydrous $Na_2SO_4$, filtered and concentrated under reduced pressure to give crude product. The crude product was purified by combi flash to afford a residue. The residue was purified by prep-TLC to give Compound 2 (42.6 mg, 0.057 mmol, 35.1% yield) as white powder.

Scheme 10: Synthetic route for Compound 9

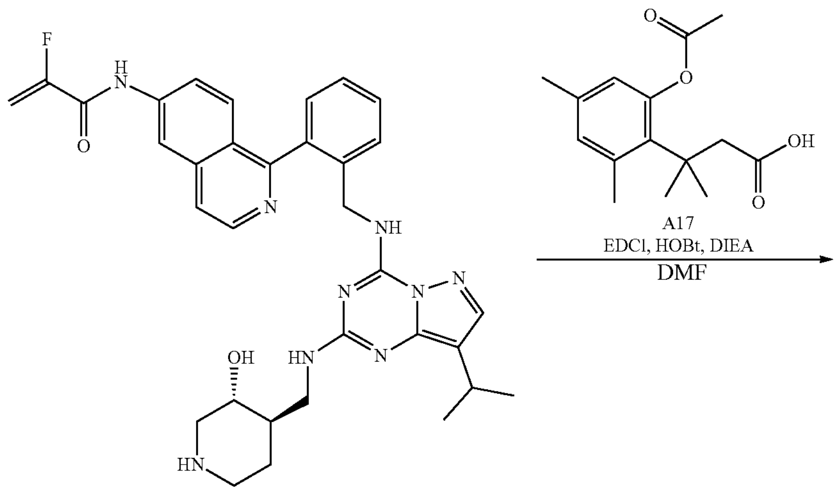

B2

A17

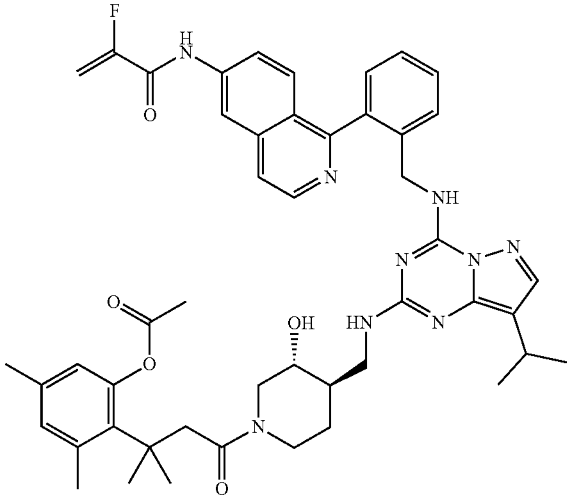

Compound 9

Procedure for Synthesis of Compound 9

To a solution of A17 (36.7 mg, 0.139 mmol, 1.0 eq) in DMF (2 mL) was added EDCI (31.99 mg, 0.166 mmol, 1.2 eq), HOBt (18.79 mg, 0.139 mmol, 1 eq), B2 (100 mg, 139.07 umol, 1 eq) and DIEA (71.89 mg, 556.27 umol, 4 eq) was added. The mixture was stirred at 20° C. for 2 hours to give a yellow mixture. LCMS showed desired product was detected. The mixture was stirred for 16 hr and then additional A17 (36.7 mg) was added, the mixture was stirred at 20° C. for 3 hr, LCMS showed the reaction was completed. The reaction mixture diluted with water 20 mL and extracted with DCM. The combined organic layers were washed with brine, dried over $Na_2SO_4$, filtered and concentrated under reduced pressure to give a residue. The residue was purified by prep-TLC to give to give Compound 9 (97.8 mg, 0.114 mmol, 82.16% yield) as white powder.

Scheme 11: Synthetic route for Compound 15

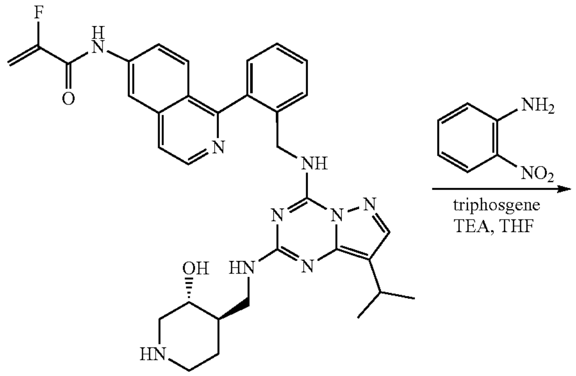

B2

-continued

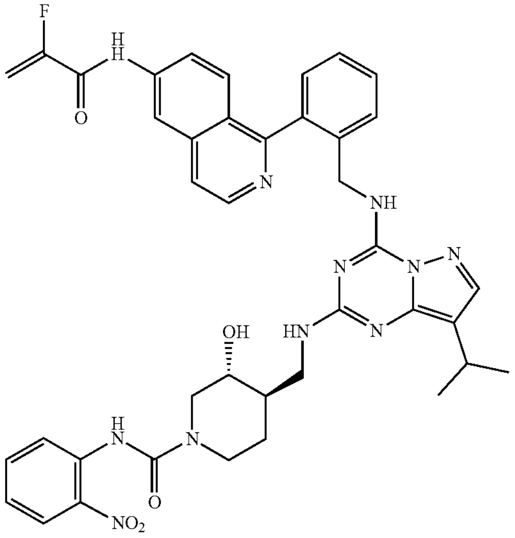

Compound 15

Procedure for Synthesis of Compound 15

The solution of 2-nitroaniline (10.56 mg, 76.49 umol) and TEA (21.11 mg, 208.60 umol, 29.03 uL) in DCM (0.5 mL) was added to a stirred solution of triphosgene (7.22 mg, 24.34 umol) in DCM (0.5 mL) at −10° C. After stirred at −10° C. for 0.5 h, the reaction was treated a solution of B2 (50 mg, 69.53 umol) and TEA (21.11 mg, 208.60 umol, 29.03 uL) in DCM (0.5 mL) at −10° C. The resultant solution was stirred at ° C. for 1 h. The solution was concentrated and then diluted with DCM (10 mL), washed with water (10 mL) and brine (10 mL×2). The organic layer was then concentrated in vacuum to give a residue. The residue was purified by prep-TLC and then lyophilized to afford compound 15 (17.2 mg, 21.94 umol, 31.55% yield) as a yellow powder.

General Schemes of Route 2

Scheme 12: Synthetic route for Compound 1

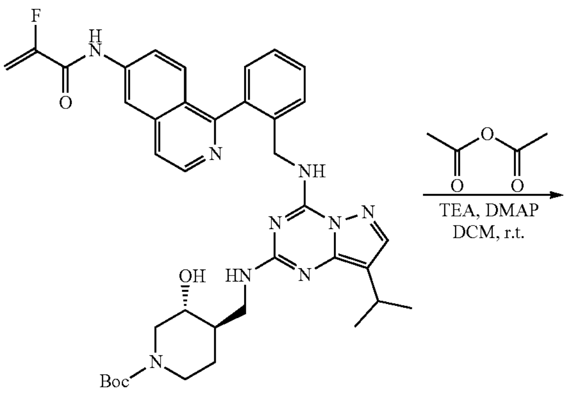

B1

-continued

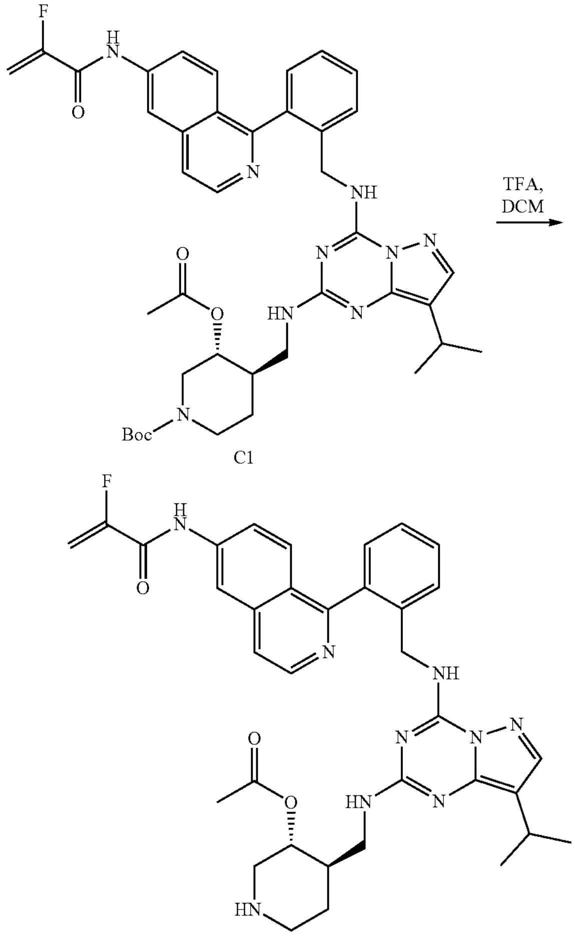

C1

Compound 1

Procedure for Synthesis of C1

To a mixture of B1 (100 mg, 0.14 mmol, 1 eq) in DCM (3 mL) was added acetic anhydride (15.82 mg, 0.154 mmol, 1.1 eq), triethylamine (28.51 mg, 0.281 mmol, 2 eq) and DMAP (8.61 mg, 0.07 mmol, 0.5 eq) at 0-5° C., the mixture was stirred at 25° C. for 1 hour to give a yellow mixture. TLC showed the reactant was consumed. The mixture was poured into $H_2O$ and extracted with EtOAc, the organic layer was washed with brine, dried over $Na_2SO_4$, filtered and concentrated under reduced pressure to give residue. The residue was purified by prep-TLC to afford C1 (103 mg, 0.137 mmol, 97.2% yield) as colorless gum.

Procedure for Synthesis of Compound 1

To a mixture of C1 (103 mg, 0.137 mmol, 1 eq) in DCM (2 mL) was added TFA (312.41 mg, 2.74 mmol, 20 eq), the mixture was stirred at 15° C. for 30 min to give a yellow mixture. LCMS showed the reactant was consumed. The mixture was concentrated under reduced pressure and treated with 1N HCl (20 uL) and lyophilized to afford Compound 1 (89.8 mg, 94.7% yield) as white powder.

Scheme 13: Synthetic route for Compound 7

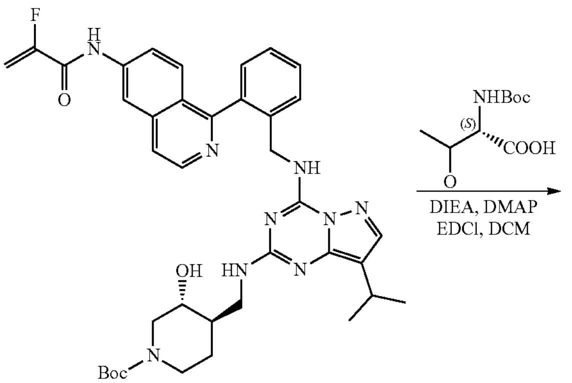

B1

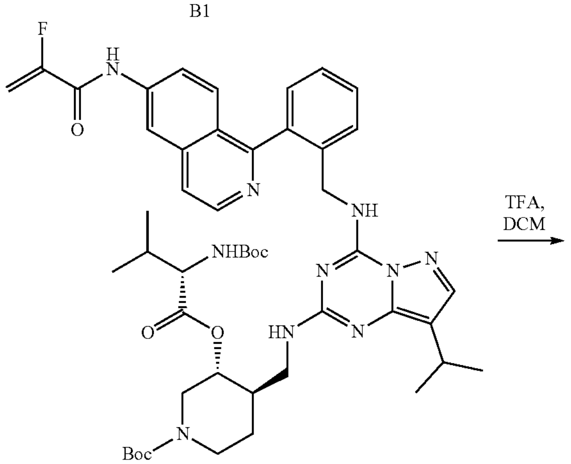

C2

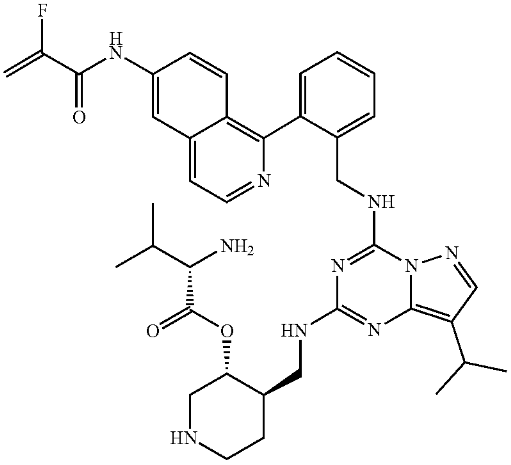

Compound 7

Procedure for Synthesis of C2

To a solution of (2S)-2-(tert-butoxycarbonylamino)-3-methyl-butanoic acid (45.91 mg, 0.211 mmol, 1.5 eq) in DCM (2 mL) was added EDCI (54.01 mg, 0.281 mmol, 2 eq), DMAP (34.42 mg, 0.281 mmol, 2 eq) and DIEA (72.83 mg, 0.563 mmol, 4 eq) at 15° C. The resulting mixture was stirred for 10 minutes and then B1 (100 mg, 0.14 mmol, 1 eq) was added. The resulting mixture was stirred at 15° C. for 5 hours to afford a colorless solution. Then it was stirred at 15° C. for other 15 hours to afford light yellow solution. Then additional (2S)-2-(tert-butoxycarbonylamino)-3-methyl-butanoic acid (45.91 mg, 0.211 mmol, 1.5 eq) and EDCI (54.01 mg, 0.281 mmol, 2 eq), DIEA (72.83 mg, 0.563 mmol, 4 eq) was added. The reaction was continued for another 15 hours. The mixture was partitioned between EtOAc and water. The organic layer was washed with brine, dried over sodium sulfate and concentrated to give the crude product as brown gum. The crude product is purified by flash column to afford C2 (50 mg, 0.55 mmol, 39% yield) as white solid.

Procedure for Synthesis of Compound 7

To a solution of C2 (50 mg, 0.055 mmol, 1 eq) in DCM (1 mL) was added TFA (154 mg, 1.35 mmol, 24.5 eq) and the mixture was stirred at 15° C. for 2 hours to afford light yellow solution. The solvent was removed under vacuum and the residue is diluted with water, treated with 1N HCl (120 uL) and lyophilized to afford Compound 7 (41-5 mg, 0.048 mmol, 87.8% yield) as light yellow solid.

TABLE 1

In-vivo PK profile by oral administration in CD-1 mice

| # Cpds | Dosing | PK Parameters | | | |
|---|---|---|---|---|---|
| | | $C_{max}$ (ng/mL) | $T_{max}$ (h) | $T_{1/2}$ (h) | $AUC_{o-t}$ (ng · h/mL) |
| Active form | $PO_1$ (30 mg/kg) | 7.02 | 0.250 | 1.74 | 14.6 |
| | $PO_2$ (100 mg/kg) | 28.3 | 0.083 | 11.6 | 93.5 |
| Compound 2 | $PO_1$ (40 mg/kg) | 1598 | 0.083 | 1.76 | 555 |
| | $PO_2$ (100 mg/kg) | 1568 | 0.083 | 1.87 | 996 |
| Compound 3 | $PO_1$ (40 mg/kg) | 900 | 0.083 | 2.83 | 397 |
| | $PO_2$ (100 mg/kg) | 1815 | 0.250 | 4.05 | 1368 |
| Compound 4 | $PO_1$ (40 mg/kg) | 616 | 0.083 | 4.39 | 282 |
| | $PO_2$ (100 mg/kg) | 1254 | 0.083 | 1.78 | 771 |
| Compound 5 | $PO_1$ (40 mg/kg) | 674 | 0.083 | 3.91 | 290 |
| | $PO_2$ (100 mg/kg) | 1368 | 0.083 | 1.62 | 967 |
| Compound 6 | $PO_1$ (40 mg/kg) | 723 | 0.083 | 5.86 | 341 |
| | $PO_2$ (100 mg/kg) | 1129 | 0.083 | 3.39 | 643 |

TABLE 2

Summarized compounds 1-20 in terms of their structures and corresponding characteristics.

| No. | Compound | Comments |
|---|---|---|
| 1 | 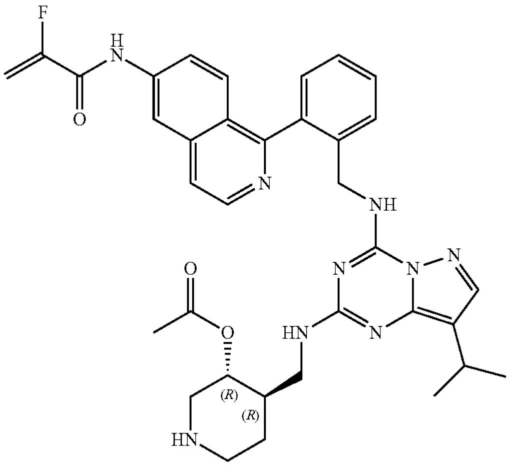 | White powder; $^1$H-NMR (400 MHz, MeOD-$d_4$) δ 8.60 (d, J = 5.2 Hz, 1 H), 8.40-8.51 (m, 1H), 8.17 (s, 1H), 7.75-7.93 (m, 3H), 7.60-7.73 (m, 2H), 7.50-7.58 (m, 2H), 5.74-5.97 (m, 1H), 5.44 (dd, J = 14.8, 3.6 Hz, 1H), 4.98-5.16 (m, 1H), 4.63-4.83 (m, 1H), 3.31-3.57 (m, 6H), 2.81-3.15 (m, 3H), 1.94-2.23 (m, 5H), 1.60-1.75 (m, 1H), 1.11-1.24 (m, 6H); MS (ESI): m/z 652.3 $[M + H]^+$. |
| 2 | 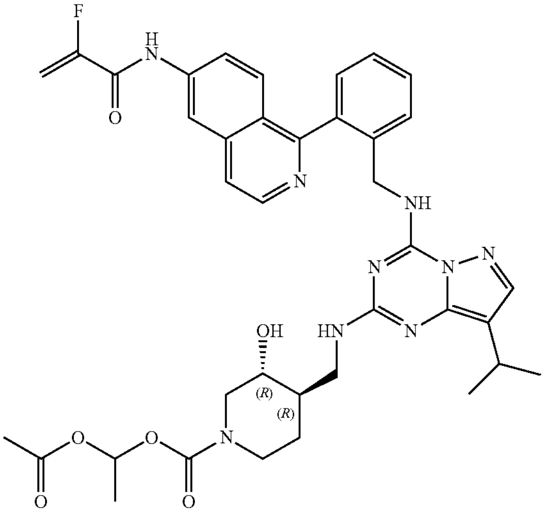 | White powder; $^1$H-NMR (400 MHz, $CDCl_3$) δ 8.57 (s, 1H) 8.30 (brd, J = 14.8 Hz, 2H), 7.34-7.77 (m, 9H), 6.77 (s, 1H), 6.53 (s, 1H), 5.76-6.01 (m, 1H), 5.32 (d, J = 14.8 Hz, 1H), 4.75-4.95 (brs, 2H), 4.05-4.45 (m, 4H), 3.25 (brs, 1H), 2.51-3.04 (m, 4H), 1.82-2.14 (m, 3H), 1.41-1.60 (m, 6H), 1.19-1.30 (m, 6H); MS (ESI): m/z 740.3 $[M + H]^+$. |
| 3 | 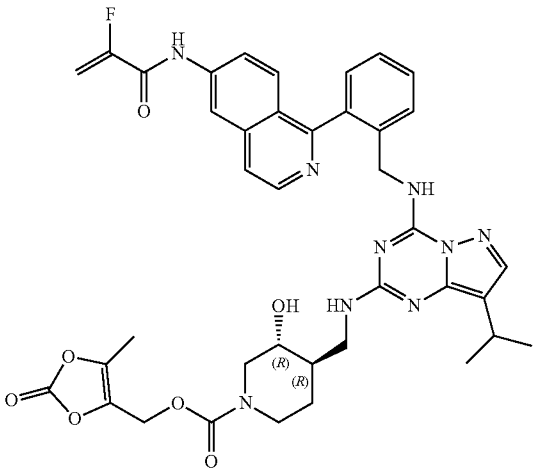 | White powder; $^1$H-NMR (400 MHz, DMSO-$d_6$) δ 10.44 (brs, 1H), 8.49-8.56 (m, 1H), 8.42-8.47 (m, 1H), 7.92-8.01 (m, 1H), 7.79-7.85 (m, 1H), 7.72-7.78 (m, 1H), 7.56-7.67 (m, 3H), 7.41-7.54 (m, 2H), 7.32-7.40 (m, 1H), 6.30 (brs, 1H), 5.68-5.88 (m, 1H), 5.45 (dd, J = 15.6, 3.6 Hz, 1H), 4.96-5.13 (m, 1H), 4.90 (s, 2H), 4.43-4.53 (m, 2H), 3.98 (brdd, J = 12.4, 4.4 Hz, 1H), 3.84 (brd, J = 12.8 Hz, 1H), 3.28-3.46 (m, 2H), 3.15-3.26 (m, 1H), 2.90 (dt, J = 13.6, 6.8 Hz, 1H), 2.71-2.81 (m, 1H), 2.56-2.66 (m, 1H), 2.14 (s, 3H), 1.62-1.72 (m, 1H), 1.50-1.62 (m, 1H), 1.23 (d, J = 6.8 Hz, 6H), 1.10-1.20 (m, 1H); MS (ESI): m/z 766.2 $[M + H]^+$. |

TABLE 2-continued

| Summarized compounds 1-20 in terms of their structures and corresponding characteristics. | | |
|---|---|---|
| No. | Compound | Comments |
| 4 | 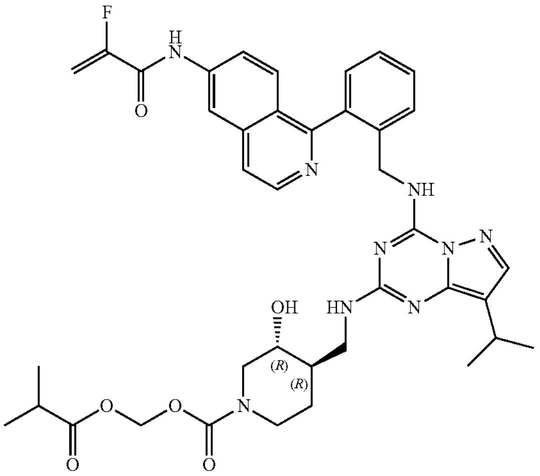 | off-white solid; $^1$H-NMR (400 MHz, DMSO-$d_6$) δ 10.43 (s, 1H), 8.52 (d, J = 5.6 Hz, 1H), 8.44 (d, J = 2.00 Hz, 1H), 7.90-8.00 (m, 1H), 7.82 (dd, J = 9.2, 2.0 Hz, 1H), 7.74 (d, J = 5.6 Hz, 1H), 7.56-7.67 (m, 3H), 7.41-7.54 (m, 2H), 7.30-7.38 (m, 1H), 6.25-6.35 (m, 1H), 5.65-5.88 (m, 3H), 5.45 (dd, J = 15.6, 3.6 Hz, 1H), 5.06 (br s, 1H), 4.47 (d, J = 5.6 Hz, 2H), 3.77-4.04 (m, 2H), 3.28-3.46 (m, 2H), 3.15-3.25 (m, 1H), 2.84-2.96 (m, 1H), 2.71-2.82 (m, 1H), 2.51-2.67 (m, 4 H), 1.50-1.73 (m, 2H),1.01-1.29 (m, 13H); MS (ESI): m/z 754.2 [M + H]$^+$. |
| 5 | 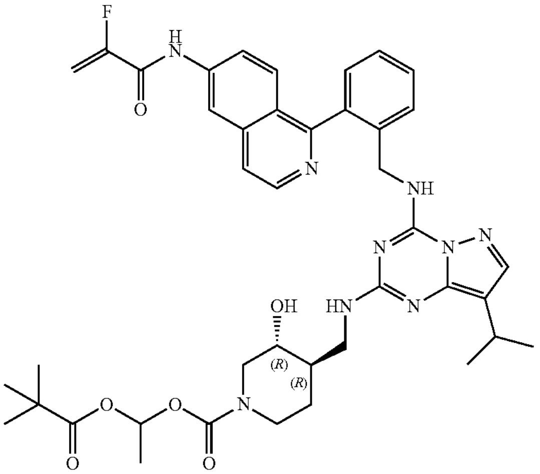 | White solid; $^1$H-NMR (400 MHz, DMSO-$d_6$) δ 10.44 (s, 1 H), 8.52 (d, J = 5.6 Hz, 1H), 8.44 (d, J = 1.6 Hz, 1H), 7.96 (s, 1H), 7.78-7.85 (m, 1H), 7.74 (d, J = 5.6 Hz, 1H), 7.54-7.65 (m, 3H), 7.41-7.53 (m, 2H), 7.35 (d, J = 7.2 Hz, 1H), 6.57-6.67 (m, 1H), 6.28 (s, 1H), 5.66-5.87 (m, 1H), 5.45 (dd, J = 15.6, 3.6 Hz, 1H), 4.96-5.14 (m, 1H), 4.46 (s, 2H), 3.96 (d, J = 13.2 Hz, 1H), 3.82 (d, J = 12.8 Hz, 1H), 3.26-3.45 (m, 2H), 3.17 (s, 1H), 2.84-2.94 (m, 1H), 2.55-2.79 (m, 2H), 1.50-1.69 (m, 2H), 1.42 (d, J = 5.2 Hz, 3H), 1.22 (d, J = 6.8 Hz, 6H), 1.09 (d, J = 5.6 Hz, 9H); LCMS: 100%, MS (ESI): m/z 782.3 [M + H]$^+$. |
| 6 | 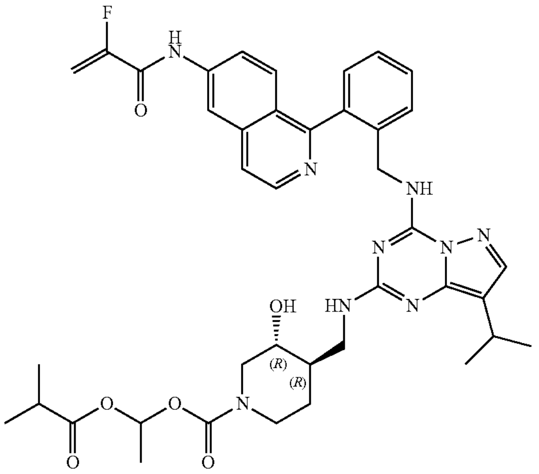 | White solid; $^1$H-NMR (400 MHz, DMSO-$d_6$) δ 10.43 (brs, 1H), 8.52 (d, J = 5.2 Hz, 1H), 8.44 (d, J = 2.0 Hz, 1H), 7.95 (brs, 1H), 7.84-7.77 (m, 1H), 7.74 (brd, J = 5.6 Hz, 1H), 7.65-7.55 (m, 3H), 7.53-7.40 (m, 2H), 7.35 (brd, J = 7.2 Hz, 1H), 6.65 (q, J = 5.2 Hz, 1H), 6.28 (brs, 1H), 5.86-5.68 (m, 1H), 5.45 (dd, J = 15.6, 3.6 Hz, 1H), 5.04 (brs, 1H), 4.46 (brs, 2H), 4.00-3.77 (m, 2H), 3.44-3.28 (m, 2H), 3.24-3.13 (m, 1H), 2.95-2.83 (m, 1H), 2.73 (brt, J = 12.0 Hz, 1H), 2.64-2.54 (m, 1H), 2.44 (brs, 2H), 1.69-1.50 (m, 2H), 1.42 (brd, J = 5.2 Hz, 3H), 1.22 (d, J = 6.8 Hz, 6H), 1.08-0.99 (m, 6H); MS (ESI): m/z 768.3 [M + H]$^+$. |

TABLE 2-continued

Summarized compounds 1-20 in terms of their structures and corresponding characteristics.

| No. | Compound | Comments |
|---|---|---|
| 7 | 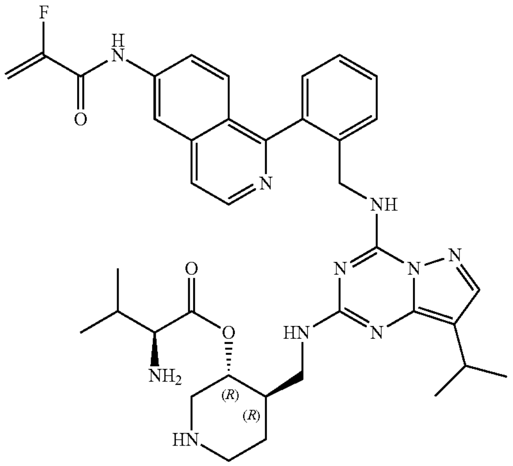 | Light yellow solid; $^1$H-NMR (400 MHz, MeOD-$d_4$) δ 8.66 (s, 1H), 8.54 (t, J = 7.2 Hz, 1H), 8.30 (d, J = 6.4 Hz, 1H), 7.96 (brt, J = 7.2 Hz, 1H), 7.83-7.94 (m, 2H), 7.66-7.75 (m, 2 H), 7.62 (brd, J = 7.2 Hz, 1H), 7.58 (d, J = 10.0 Hz, 1H), 5.95 (d, J = 3.63 Hz, 1 H) 5.84 (d, J = 3.63 Hz, 1 H) 5.48 (dd, J = 14.88, 3.6 Hz, 1H), 5.18-5.33 (m, 2H), 4.67-4.84 (m, 1 H), 4.14 (t, J = 5.2 Hz, 1H), 3.63-3.80 (m, 2H), 3.37-3.63 (m, 2H), 3.10-3.31 (m, 2H), 2.80-2.95 (m, 1H), 2.30-2.51 (m, 2H), 2.04-2.22 (m, 1H), 1.75-1.94 (m, 1H), 1.19-1.26 (m, 6H), 1.14 (brdd, J = 12.4, 6.8 Hz, 6H); MS (ESI): m/z 709.3 [M + H]$^+$. |
| 8 | 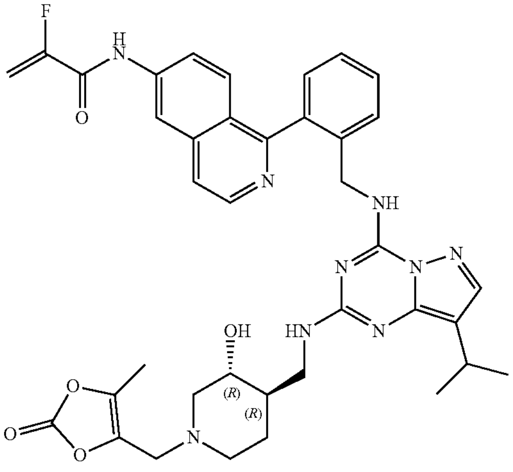 | Off-white solid; $^1$H-NMR (400 MHz, DMSO-$d_6$) δ 10.43 (s, 1H), 8.52 (d, J = 5.6 Hz, 1H), 8.44 (d, J = 2.0 Hz, 1H), 7.94 (brs, 1H), 7.81 (dd, J = 8.8, 2.0 Hz, 1H), 7.76 (d, J = 5.8 Hz, 1H), 7.63 (d, J = 9.0 Hz, 1H), 7.56-7.61 (m, 2H), 7.47-7.53 (m, 1H), 7.42-7.47 (m, 1H), 7.33-7.37 (m, 1 H), 6.25 (brs, 1 H), 5.70-5.87 (m, 1H), 5.46 (dd, J = 15.6, 3.6 Hz, 1H), 4.79 (brs, 1H), 4.47 (brs, 2H), 3.22-3.43 (m, 5H), 2.82-2.96 (m, 2H), 2.73 (m, 1H), 2.10 (s, 3H), 1.97 (m, 1H), 1.85 (m, 1H), 1.61 (m, 1H), 1.25-1.39 (m, 2H), 1.22 (d, J = 6.8 Hz, 6H); MS (ESI): m/z 722.2 [M + H]$^+$. |
| 9 | 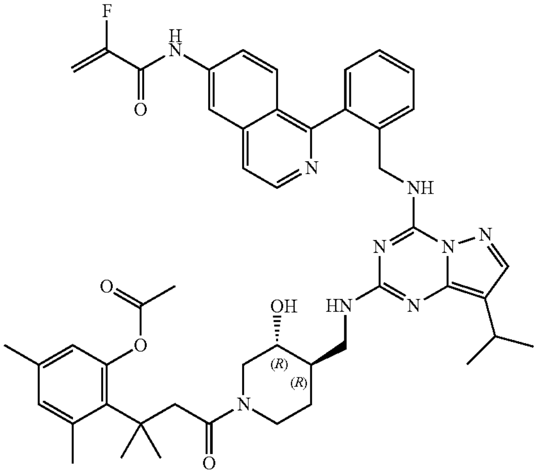 | White powder; $^1$H-NMR (400 MHz, DMSO-$d_6$) δ 10.44 (s, 1H), 8.52 (d, J = 6.0 Hz, 1H), 8.44 (d, J = 1.6 Hz, 1H), 7.96 (s, 1H), 7.81 (dd, J = 9.2, 2.0 Hz, 1H), 7.74 (d, J = 6.0 Hz, 1H), 7.55-7.66 (m, 3H), 7.41-7.51 (m, 2H), 7.32-7.38 (m, 1H), 6.73 (s, 1H), 6.54 (s, 1H), 6.25 (s, 1H), 5.68-5.91 (m, 1H), 5.45 (dd, J = 15.6, 3.6 Hz, 1H), 4.96 (s, 1H), 4.47 (d, J = 5.2 Hz, 2H), 3.30-3.38 (m, 1H), 2.89 (m, 1H), 2.80 (s, 2H), 2.46 (s, 3H), 2.20 (s, 3H) 2.13 (s, 3H), 1.52-1.63 (m, 2H) 1.47 (s, 6H) 1.22 (d, J = 6.8 Hz, 6H) 0.69-1.11 (m, 1H); MS (ESI): m/z 865.5 [M + H]$^+$. |

TABLE 2-continued

| Summarized compounds 1-20 in terms of their structures and corresponding characteristics. | | |
|---|---|---|
| No. | Compound | Comments |
| 10 | 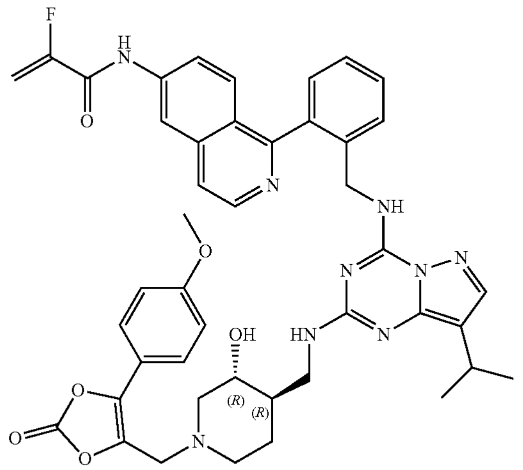 | White solid; $^1$H-NMR (400 MHz, DMSO-$d_6$) δ 10.42 (s, 1H), 8.51 (d, J = 5.6 Hz, 1H), 8.43 (d, J = 1.6 Hz, 1H), 7.93 (s, 1H), 7.79 (dd, J = 9.2, 2.0 Hz, 1H), 7.74 (d, J = 6.0 Hz, 1H), 7.52-7.64 (m, 5H), 7.39-7.51 (m, 2H), 7.34 (d, J = 7.6 Hz, 1H), 7.05 (d, J = 8.4 Hz, 2H), 6.25 (s, 1H) 5.67-5.86 (m, 1H), 5.44 (dd, J = 15.2, 3.6 Hz, 1H), 4.79 (s, 1H), 4.46 (s, 2H), 3.81 (s, 3H), 3.56 (s, 2H), 3.24-3.37 (m, 3H), 2.99 (m, 1H), 2.88 (m, 1H), 2.80 (m, 1H), 2.00 (t, J = 10.4 Hz, 1H), 1.90 (t, J = 10.0 Hz, 1H), 1.60 (d, J = 13.6 Hz, 1H), 1.34 (s, 1H), 1.26 (s, 1H), 1.21 (d, J = 6.8 Hz, 6H); MS (ESI): m/z 814.4 $[M + H]^+$. |
| 11 | 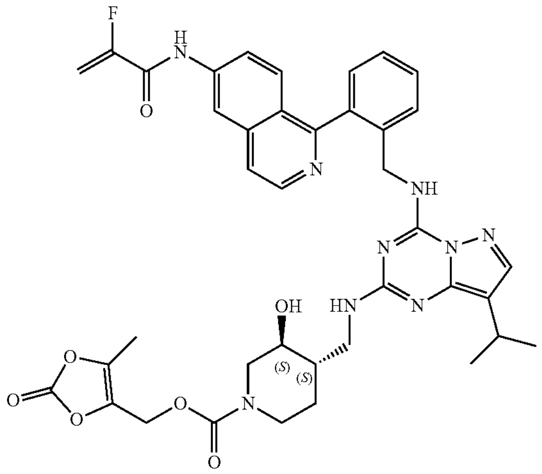 | white powder; $^1$H-NMR (400 MHz, DMSO-$d_6$) δ 10.67 (brs, 1H), 8.53 (s, 1H), 8.48 (d, J = 6.0 Hz, 1H), 7.95 (brs, 1H), 7.84 (brd, J = 9.6 Hz, 1H), 7.64-7.70 (m, 2H), 7.49-7.63 (m, 3H), 7.39-7.45 (m, 1H), 5.72-5.93 (m, 1H), 5.51 (dd, J = 15.6, 4.0 Hz, 1H), 4.92 (s, 2H), 4.59 (brs, 2H), 4.02 (m, 1H), 3.85 (m, 1H), 2.85-2.90 (m, 1H), 2.73 (brs, 1 H), 2.57-2.63 (m, 1H), 2.16 (s, 3H), 1.55 (brs, 2H), 1.20 (d, J = 6.8 Hz, 6H), 1.02-1.13 (m, 1H); MS (ESI): m/z 766.2 $[M + H]^+$. |
| 12 | 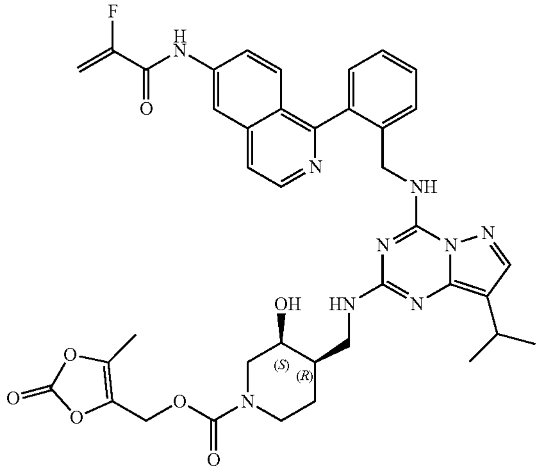 | White powder; $^1$H-NMR (400 MHz, DMSO-$d_6$) δ 10.43 (s, 1H) 8.51 (d, J = 6.0 Hz, 1H), 8.43 (s, 1H), 7.93 (s, 1H), 7.81 (dd, J = 9.2, 2.0 Hz, 1H), 7.74 (d, J = 5.6 Hz, 1H), 7.55-7.64 (m, 3H), 7.41-7.53 (m, 2H), 7.35 (d, J = 6.0 Hz, 1H), 6.27 (s, 1H), 5.67-5.89 (m, 1H), 5.45 (dd, J = 15.2, 3.6 Hz, 1H), 4.88 (s, 2H), 4.60 (s, 1H), 4.46 (d, J = 6.0 Hz, 2H), 3.91-3.93 (m, 2H), 3.68 (s, 1H), 3.18-3.30 (m, 1H), 2.86-2.91 (m, 2H), 2.72-2.79 (m, 1H), 2.15 (s, 3H), 1.73 (s, 1H), 1.46-1.58 (m, 1H), 1.30-1.34 (m, 1H), 1.22 (dd, J = 7.2, 2.0 Hz, 6H); MS (ESI): m/z 766.2 $[M + H]^+$. |

TABLE 2-continued

Summarized compounds 1-20 in terms of their structures and corresponding characteristics.

| No. | Compound | Comments |
|---|---|---|
| 13 | 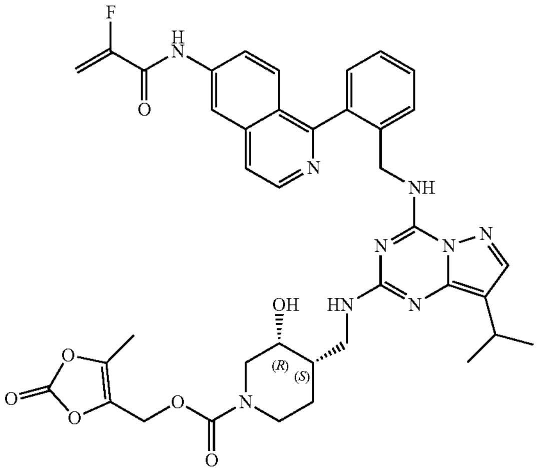 | White powder; $^1$H-NMR (400 MHz, DMSO-$d_6$) δ 10.45 (s, 1H), 8.51 (d, J = 6.0 Hz, 1H), 8.43 (s, 1H), 7.95 (s, 1H), 7.81 (dd, J = 9.2, 2.0 Hz, 1H), 7.74 (d, J = 5.6 Hz, 1H), 7.55-7.66 (m, 3H), 7.42-7.54 (m, 2H), 7.35 (d, J = 6.8 Hz, 1H), 6.28 (s, 1H), 5.69-5.93 (m, 1H), 5.45 (dd, J = 15.6, 3.6 Hz, 1H), 4.87 (s, 2H), 4.62 (s, 1H), 4.46 (d, J = 4.8 Hz, 2H), 3.90-3.94 (m, 2H), 3.67 (s, 1H), 3.17-3.30 (m, 1H), 2.84-2.90 (m, 2H), 2.70-2.81 (m, 1H), 2.15 (s, 3H), 1.67-1.80 (m, 1H), 1.43-1.57 (m, 1H), 1.32 (d, J = 14.4 Hz, 1H), 1.21 (dd, J = 7.2, 2.0 Hz, 6H); MS (ESI): m/z 766.2 $[M + H]^+$. |
| 14 | 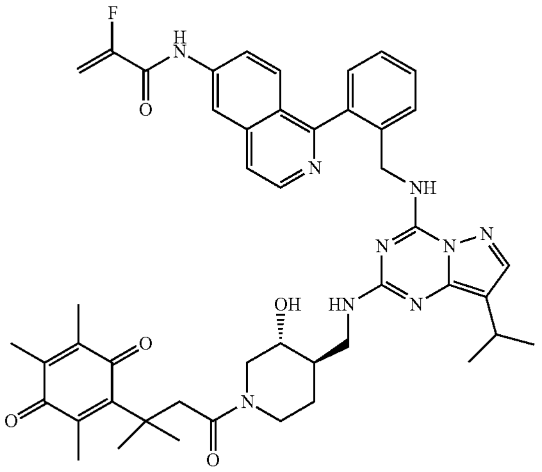 [SMILES: C=C(F)C(=O)Nc1ccc2c(-c3ccccc3CNc3nc(NC[C@H]4CCN(C(=O)CC(C)(C)C5=C(C)C(=O)C(C)=C(C)C5=O)C[C@@H]4O)nc4c(C(C)C)cnn34)nccc2c1] | Yellow solid; $^1$H NMR (400 MHz, DMSO-$d_6$) δ 10.47 (1 H, br s) 8.52 (1 H, d, J = 5.77 Hz) 8.44 (1 H, d, J = 2.01 Hz) 8.00 (1 H, br s) 7.82 (1 H, dd, J = 9.03, 2.01 Hz) 7.75 (1 H, d, J = 5.77 Hz) 7.63 (1 H, d, J = 9.03 Hz) 7.56-7.65 (1 H, m) 7.57 (1 H, s) 7.42-7.52 (1 H, m) 7.41-7.53 (1 H, m) 7.33-7.37 (1 H, m) 6.31 (1 H, br s) 5.71-5.86 (1 H, m) 5.46 (1 H, dd, J = 15.56, 3.76 Hz) 5.07 (1 H, s) 4.46 (2 H, br s) 3.16-3.45 (8 H, m) 2.85-2.94 (1 H, m) 2.04 (3 H, s) 1.83-1.87 (1 H, m) 1.78 (3 H, s) 1.52-1.70 (2 H, m) 1.36 (6 H, s) 1.27 (2 H, s) 1.22 (7 H, d, J = 7.03 Hz); MS (ESI): m/z 841.9 [M + H]+ |
| 15 | 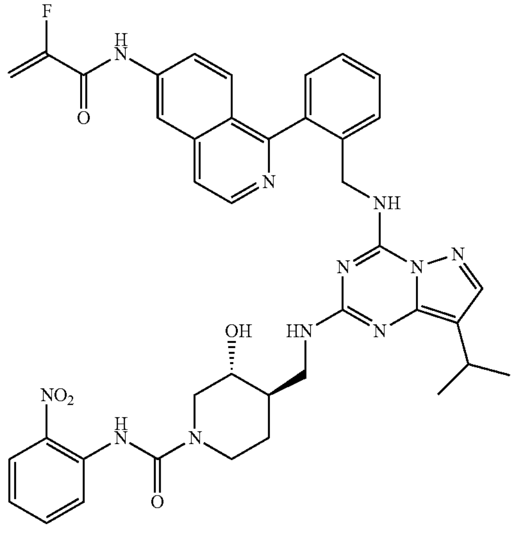 [SMILES: C=C(F)C(=O)Nc1ccc2c(-c3ccccc3CNc3nc(NC[C@H]4CCN(C(=O)Nc5ccccc5[N+](=O)[O-])C[C@@H]4O)nc4c(C(C)C)cnn34)nccc2c1] | Yellow powder; $^1$H NMR (400 MHz, DMSO-$d_6$) δ 10.46 (1 H, br s), 9.27 (1 H, br s), 8.52 (1 H, d, J = 8.0 Hz), 8.44 (1 H, d, J = 2.0 Hz), 7.98 (2 H, dd, J = 8.0, 1.6 Hz), 7.90 (1 H, d, J = 8.0 Hz), 7.81 (1 H, dd, J = 8.0, 4.0 Hz), 7.74 (1 H, d, J = 4.0 Hz), 7.56-7.65 (4 H, m), 7.47-7.52 (1 H, m), 7.43 (1 H, t, J = 7.6 Hz), 7.35 (1 H, d, J = 8.0 Hz), 7.12-7.22 (1 H, m), 6.31-6.40 (1 H, m), 5.77 (1 H, dd, J = 48.0, 4.0 Hz), 5.45 (1 H, dd, J = 16.0, 4.0 Hz), 5.11 (1 H, br s), 4.41-4.52 (2 H, m), 4.07 (1 H, br dd, J = 12.0, 4.0 Hz), 3.93 (1 H, d, J = 16.0 Hz), 3.26-3.51 (3 H, m), 2.78-2.94 (2 H, m), 2.64-2.73 (1 H, m), 1.56-1.80 (2 H, m), 1.19-1.28 (7 H, m); MS (ESI): m/z 774.3 [M + H]+ |

TABLE 2-continued

Summarized compounds 1-20 in terms of their structures and corresponding characteristics.

| No. | Compound | Comments |
| --- | --- | --- |
| 16 | 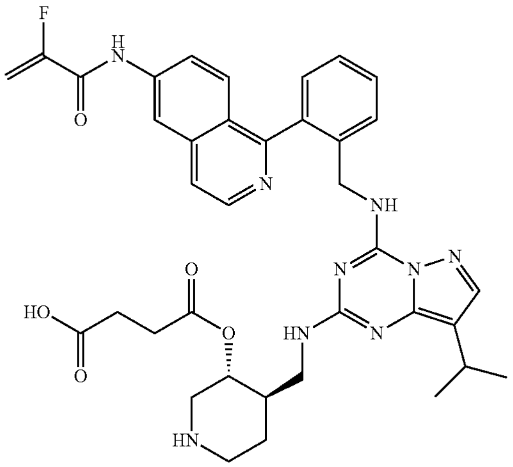 [SMILES: C=C(F)C(=O)Nc1ccc2c(-c3ccccc3CNc3nc(NC[C@H]4CCNC[C@@H]4OC(=O)CCC(=O)O)nc4c(C(C)C)cnn34)nccc2c1] | White solid; $^{1}$H NMR (400 MHz, DMSO-$d_6$) δ 10.88 (s, 1H), 9.49 (m, 2H), 8.60 (s, 1H) 8.49 (d, J = 5.77 Hz, 1H), 8.12 ( d, J = 6.40 Hz, 1H), 7.85 (d, J = 9.20 Hz, 1H), 7.75 (m, 1H), 7.53-7.62 (m, 3H), 7.42-7.52 (m, 2H), 5.45 (dd, J = 15.56, 3.76 Hz, 1 H) 4.91 (m, 2 H) 3.10-3.62 (m, 5H), 2.76-3.0 (m, 3H), 2.61 (m, 3H), 2.44 (m, 1H), 1.85-2.10 (m, 2H), 1.62 (m, 1H), 1.23 (d, J = 6.78 Hz, 6 H); MS (ESI): m/z 710.0 [M + H]+ |
| 17 | 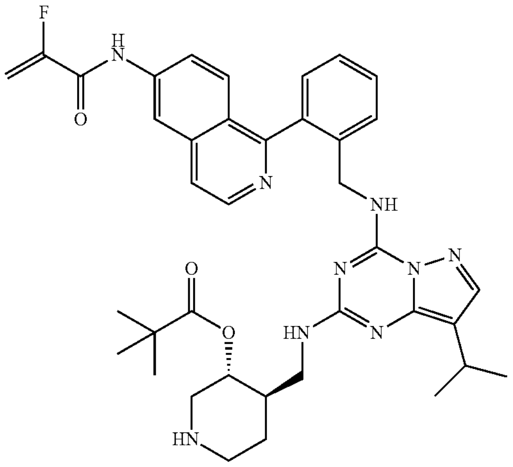 [SMILES: C=C(F)C(=O)Nc1ccc2c(-c3ccccc3CNc3nc(NC[C@H]4CCNC[C@@H]4OC(=O)C(C)(C)C)nc4c(C(C)C)cnn34)nccc2c1] | white solid; $^{1}$H NMR (400 MHz, DMSO-$d_6$) δ 10.55 (s, 1H), 8.63 (m, 2H) 8.49 (m, 3H), 8.15 (m, , 1H), 7.85 (m, 2H), 9.60-7.70 (m, 3H), 7.55 (m, 1H), 7.48 (m, 1H), 7.40 (m, 1H), 5.40-5.90 (m, 1H), 5.48 (dd, J = 15.56, 3.76 Hz, 1 H), 4.81 (m, 1 H), 4.47 (m, 2H), 3.35 (m, 1H), 3.23 (m, 1H), 3.05 (m, 1H), 2.75-2.95 (m, 3H), 1.85-2.15 (m, 2H), 1.50 (m, 1H), 1.1-1.3 (m, 15 H); MS (ESI): m/z 694 [M + H]+ |
| 18 | 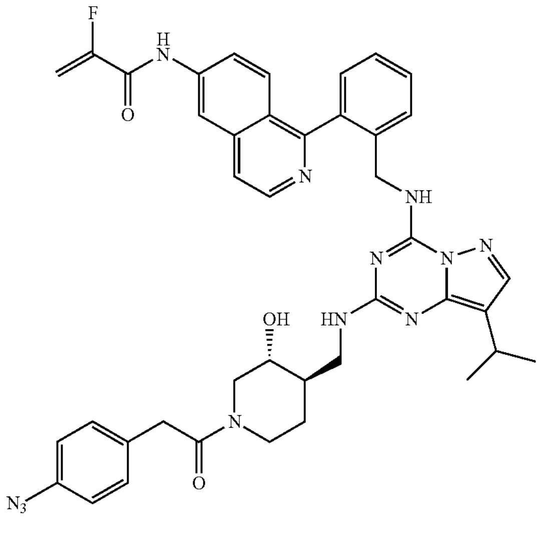 [SMILES: C=C(F)C(=O)Nc1ccc2c(-c3ccccc3CNc3nc(NC[C@H]4CCN(C(=O)Cc5ccc(N=[N+]=[N-])cc5)C[C@@H]4O)nc4c(C(C)C)cnn34)nccc2c1] | white solid; $^{1}$H NMR (400 MHz, DMSO-$d_6$) δ 10.47 (s, 1 H) 8.52 (d, J = 5.77 Hz, 1 H) 8.45 (d, J = 2.01 Hz, 1 H) 8.00 (br s, 1 H) 7.82 (dd, J = 9.16, 2.13 Hz, 1 H) 7.75 (d, J = 5.77 Hz, 1 H) 7.63 (d, J = 9.29 Hz, 1 H) 7.56-7.61 (m, 2 H) 7.50 (td, J = 7.53, 1.51 Hz, 1 H) 7.41-7.47 (m, 1 H) 7.33-7.38 (m, 1 H) 7.25 (d, J = 8.53 Hz, 2 H) 7.00 (d, J = 8.53 Hz, 2 H) 6.30 (br s, 1 H) 5.68-5.89 (m, 1 H) 5.46 (dd, J = 15.56, 3.76 Hz, 1 H) 5.03 (br s, 1 H) 4.47 (br d, J = 5.27 Hz, 2 H) 3.77-4.32 (m, 1 H) 3.68 (m, 2 H) 3.35 (m, 2 H) 3.10-3.16 (m, 1 H) 3.05 (m, 2 H) 2.89 (dt, J = 13.74, 6.81 Hz, 1 H) 2.53 (m, 1 H) 1.51-1.70 (m, 2 H) 1.22 (d, J = 6.78 Hz, 6 H) 1.05 (m, 1 H); MS (ESI): 769.3 m/z [M + H]+ |

TABLE 2-continued

Summarized compounds 1-20 in terms of their structures and corresponding characteristics.

| No. | Compound | Comments |
| --- | --- | --- |
| 19 | 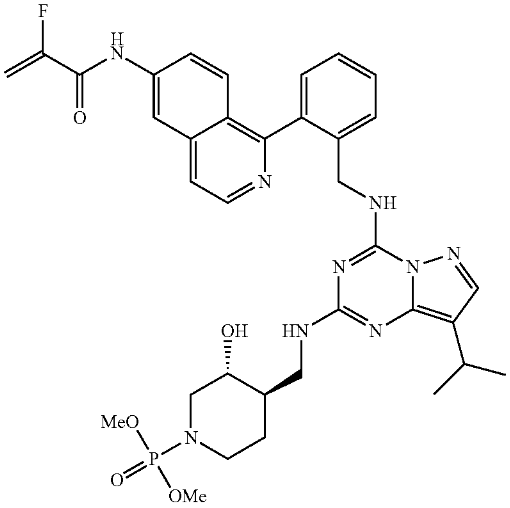 [SMILES: C=C(F)C(=O)Nc1ccc2c(-c3ccccc3CNc3nc(NC[C@H]4CCN(P(=O)(OC)OC)C[C@@H]4O)nc4c(C(C)C)cnn34)nccc2c1] | White solid; $^1$H NMR (400 MHz, MeOD) δ 8.33-8.41 (1 H, m) 8.23-8.33 (1 H, m) 7.61-7.67 (2 H, m) 7.43-7.60 (4 H, m) 7.39 (1 H, d, J = 15.2 Hz) 7.34 (1 H, d, J = 7.6 Hz) 5.69-5.87 (1 H, m) 5.36 (1 H, dd, J = 15.2, 3.2 Hz) 4.88-5.09 (2 H, m) 4.59 (1 H, s) 4.27 (1 H, s) 3.60-3.74 (6 H, m) 3.54 (1 H, s) 3.41 (1 H, s) 3.02-3.28 (2 H, m) 2.50-2.90 (2 H, m) 2.49-2.78 (2 H, m) 1.69 (1 H, s) 1.51 (2 H, s) 1.13-1.22 (6 H, m); MS (ESI): m/z 718.3 [M + H]+ |
| 20 | 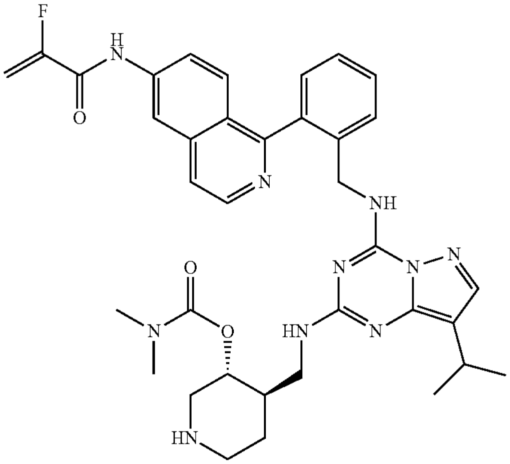 [SMILES: C=C(F)C(=O)Nc1ccc2c(-c3ccccc3CNc3nc(NC[C@H]4CCNC[C@@H]4OC(=O)N(C)C)nc4c(C(C)C)cnn34)nccc2c1] | white solid; $^1$H NMR (400 MHz, DMSO-d6) δ 10.58 (1 H, br s) 8.52 (1 H, d, J = 5.77 Hz) 8.46 (1 H, d, J = 1.76 Hz) 7.97 (1 H, br s) 7.87 (1 H, dd, J = 9.16, 2.13 Hz) 7.75 (1 H, d, J = 5.77 Hz) 7.55-7.65 (3 H, m) 7.41-7.52 (2 H, m) 7.35 (1 H, dd, J = 7.40, 1.38 Hz) 6.24 (1 H, br s) 5.78-5.91 (1 H, m) 5.46 (1 H, dd, J = 15.81, 3.76 Hz) 4.34-4.50 (3 H, m) 3.49 (1 H, br s) 3.17 (2 H, br dd, J = 11.92, 4.39 Hz) 2.98-3.03 (1 H, m) 2.89 (2 H, dt, J = 13.87, 7.00 Hz) 2.80 (6 H, s) 1.96-2.08 (1 H, m) 1.82-1.94 (1 H, m) 1.72 (1 H, br s) 1.26 (2 H, s) 1.22 (6 H, d, J = 7.03 Hz); MS (ESI): m/z 681.3 [M + H]+ |

The invention claimed is:

1. A compound having the general formula I

Formula I

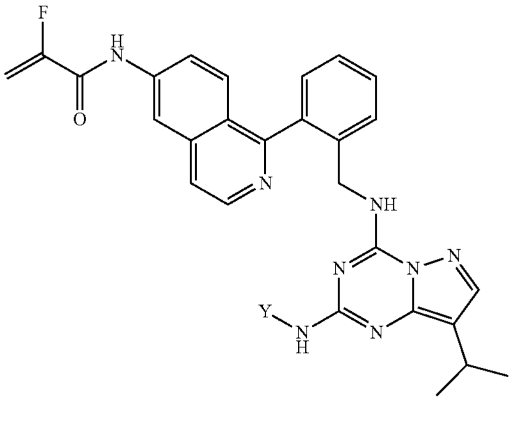

wherein

Y is, at each occurrence, independently selected from

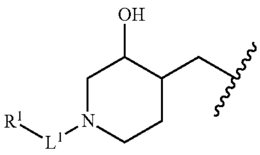

and

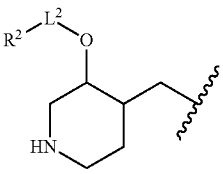

;

$L^1$ and $L^2$ are, at each occurrence, independently selected from the group consisting of $-CH_2-$, $-CH(CH_3)-$, $-(C{=}O)-$, $-(C{=}O)NH-$, $-(C{=}O)O-$, $-(C{=}O)OCH_2-$, $-(C{=}O)OCH(CH_3)-$, $-(C{=}O)CH_2-$, $-(C{=}O)CH_2C(CH_3)_2-$, $-O(SO_2)OCH_2C(CH_3)_2-$, $-P({=}O)OH-$ and $-C(CH_3)'CH-$;

or $L^1$ is absent;

$R^1$ is, at each occurrence, independently selected from the group consisting of $-OH$, $-O(C{=}O)R^3$, $-O(C{=}O)$ OR$^3$, —(C═O)R$^3$, aryl substituted with —NO$_2$ or —N$_3$, and any structure of the following Group A;

Group A

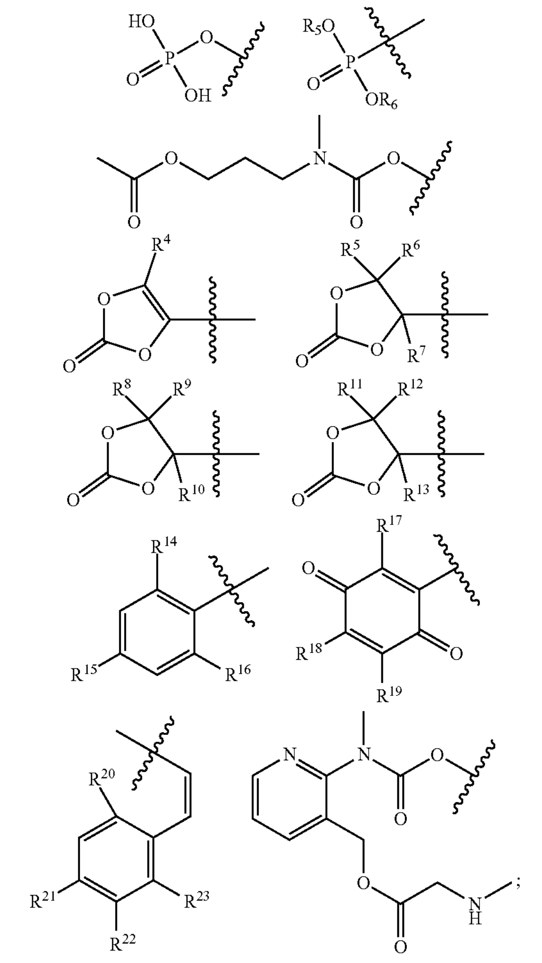

wherein L$^1$ is only absent if R1 is

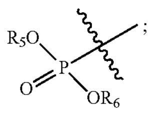

R$^2$ is, at each occurrence, independently selected from the group consisting of —OH, —O(C═O)R$^{24}$, —NR$^{25}$R$^{26}$, C1-C11 alkyl, C1-C6 alkyl substituted with —OH, —(C═O)OH or NH$_2$, heterocyclyl substituted with heterocycle, and any structure of the following Group B;

Group B

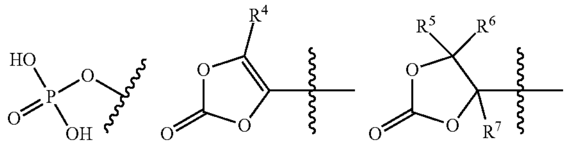

-continued

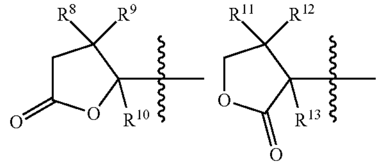

R$^3$ is, at each occurrence, independently selected from the group consisting of C1-C6 alkyl, C1-C6 alkyl substituted with alkoxy, and C3-C10 cycloalkyl;

R$^4$ is, at each occurrence, independently selected from the group consisting of C1-C3 alkyl, phenyl, phenyl substituted with C1-C3 alkyl and phenyl substituted with C1-C3 alkoxy;

R$^5$, R$^6$, R$^7$, R$^8$, R$^9$, R$^{10}$, R$^{11}$, R$^{12}$ and R$^{13}$ are, at each occurrence, independently selected from hydrogen and C1-C6 alkyl;

R$^{14}$ and R$^{20}$ are, at each occurrence, independently selected from the group consisting of hydrogen, —O(C═O)R$^{27}$, and —NO$_2$;

R$^{15}$, R$^{16}$, R$^{17}$, R$^{18}$, R$^{19}$, R$^{21}$, R$^{22}$ and R$^{23}$ are, at each occurrence, independently selected from the group consisting of hydrogen, C1-C6 alkyl, —NO$_2$, and —N$_3$;

R$^{24}$ is, at each occurrence, independently selected from the group consisting of C1-C6 alkyl and C3-C10 cycloalkyl;

R$^{25}$, R$^{26}$ and R$^{27}$ are C1-C6 alkyl;

wherein when Y is

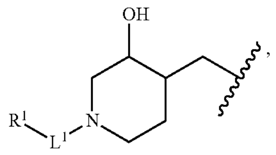

R$^1$ is, at each occurrence, independently selected from the group consisting of —O(C═O)R$^3$, aryl substituted with —NO$_2$ or N$_3$, and any structure of the following Group C Group C

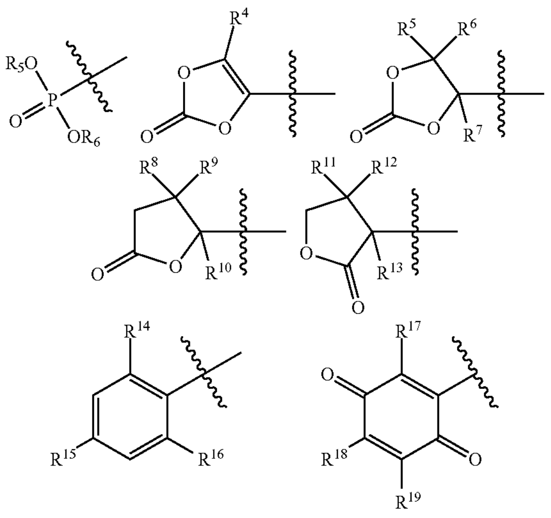

-continued

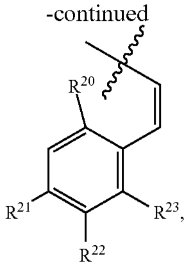

or wherein when Y is

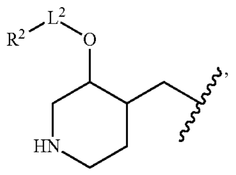

$L^2$ is —(C═O)—, $R^2$ is, at each occurrence, independently selected from the group consisting of —O(C═O)$R^{24}$, —N$R^{25}R^{26}$, C1-C11 alkyl, C1-C6 alkyl substituted with —(C═O)OH, and $NH_2$, and any structure of the following Group E Group E

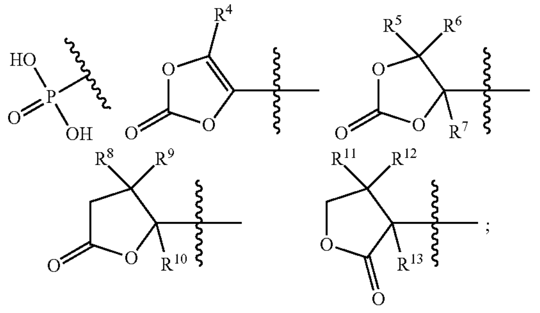

or an enantiomer, stereoisomeric form, mixture of enantiomers, diastereomer, mixture of diastereomer, racemate of the above mentioned compounds or a pharmaceutically acceptable salt thereof.

2. The compound according to claim 1, wherein Y is

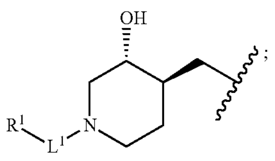

$L^1$ is, at each occurrence, independently selected from the group consisting of —$CH_2$— and (C═O)O$CH_2$—;

$R^1$ is any structure of the following Group D;

Group D

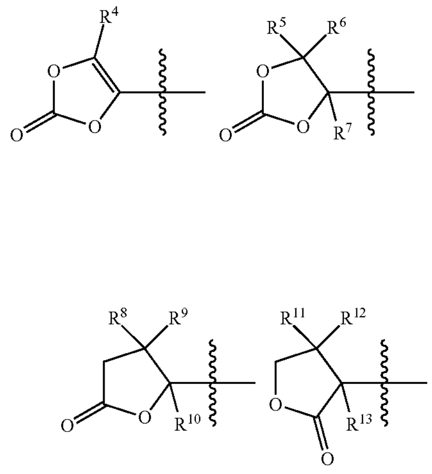

wherein $R^4$, $R^5$, $R^6$, $R^7$, $R^8$, $R^9$, $R^{10}$, $R^{11}$, $R^{12}$ and $R^{13}$ are as defined in claim 1;

or an enantiomer, stereoisomeric form, mixture of enantiomers, diastereomer, mixture of diastereomer, racemate of the above mentioned compounds or a pharmaceutically acceptable salt thereof.

3. The compound according to claim 1, wherein Y is

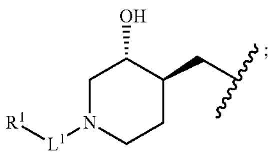

$L^1$ is, at each occurrence, independently selected from the group consisting of —$CH_2$— and —(C═O)O$CH_2$—;

$R^1$ is

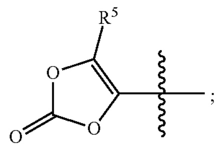

wherein $R^5$ is as defined in claim 1; or an enantiomer, stereoisomeric form, mixture of enantiomers, diastereomer, mixture of diastereomers, racemate of the above mentioned compounds or a pharmaceutically acceptable salt thereof.

4. The compound according to claim 1, wherein said compound is any one of the compounds 1-20, as defined in the following table:

| No. | compound |
| --- | --- |
| 1 | 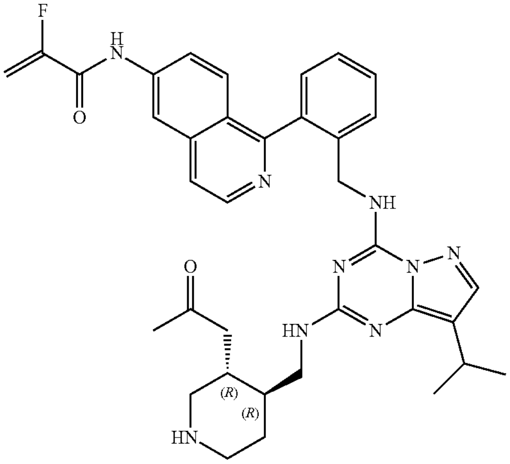 |
| 2 | 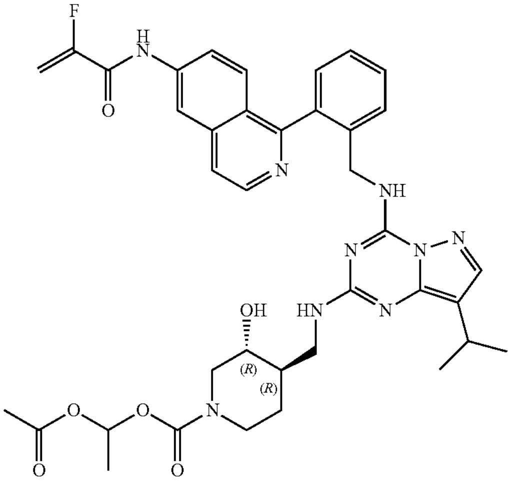 |
| 3 | 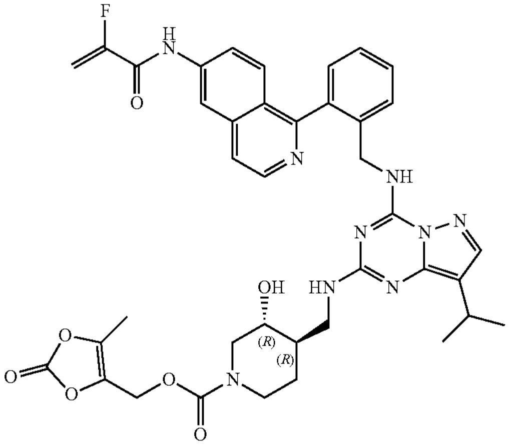 |
-continued
| No. | compound |
| --- | --- |
| 4 | 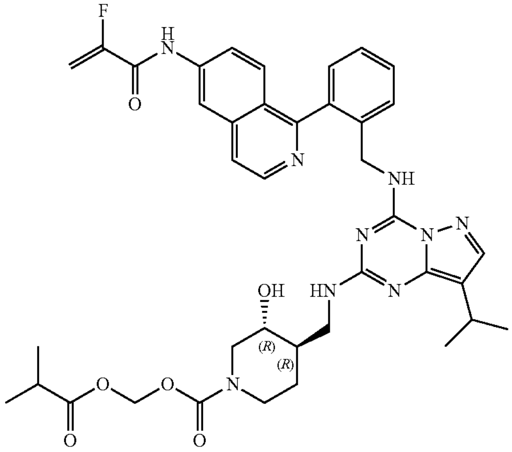 |
| 5 | 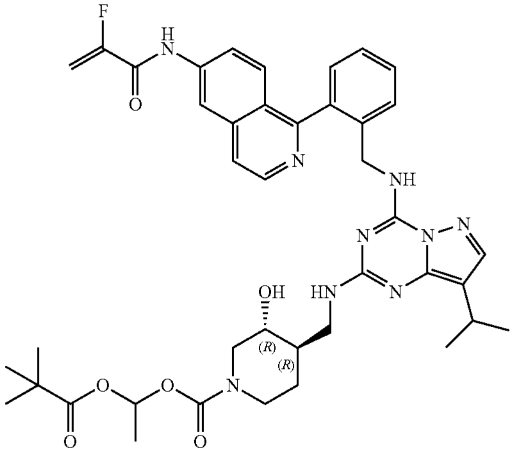 |
| 6 | 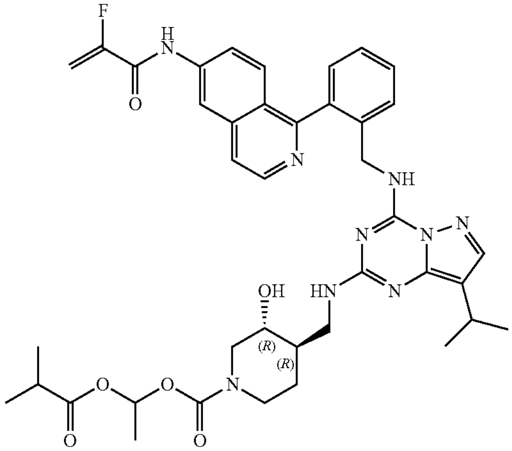 |

-continued
| No. | compound |
|---|---|
| 7 | 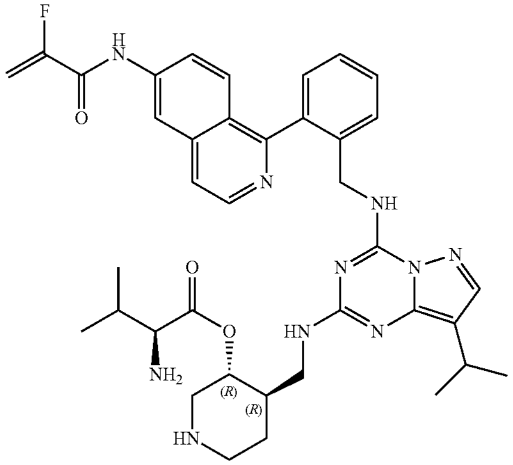 |
| 8 | 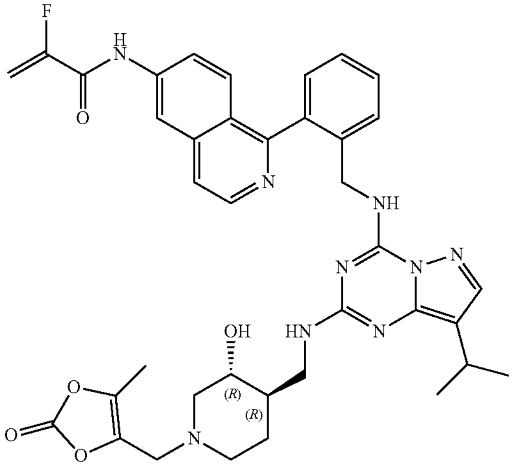 |
| 9 | 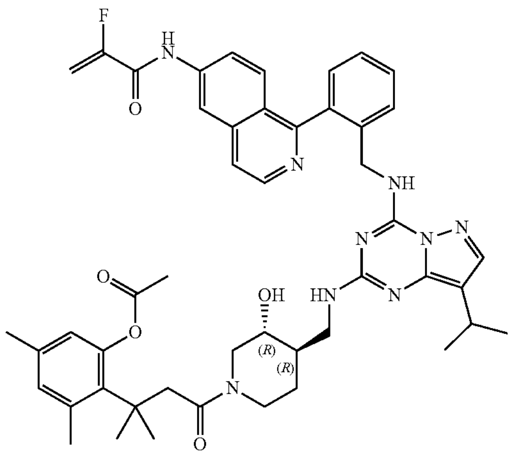 |
-continued
| No. | compound |
|---|---|
| 10 | 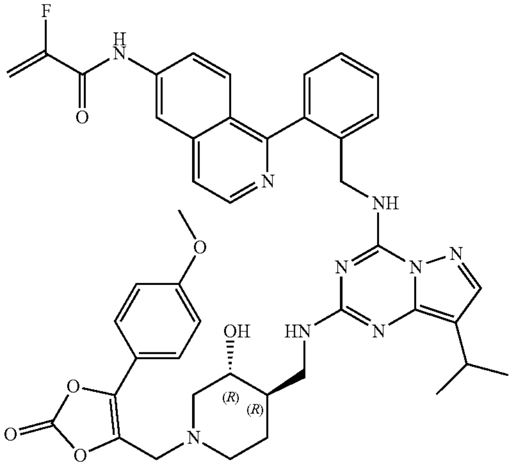 |
| 11 | 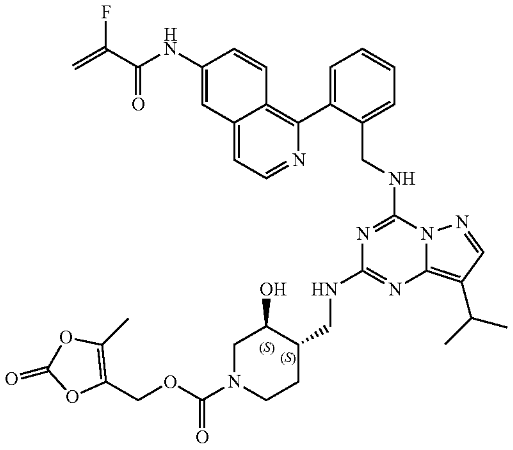 |
| 12 | 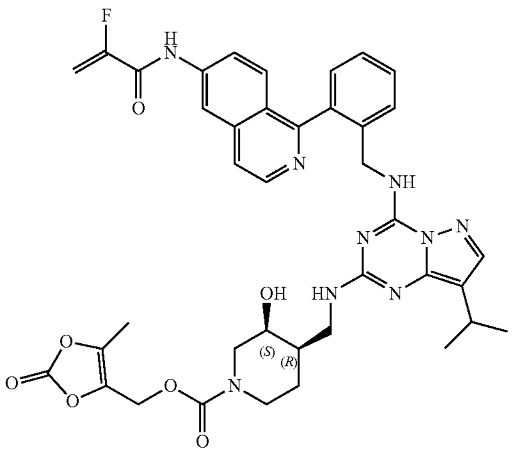 |

-continued
| No. | compound |
|---|---|
| 13 | 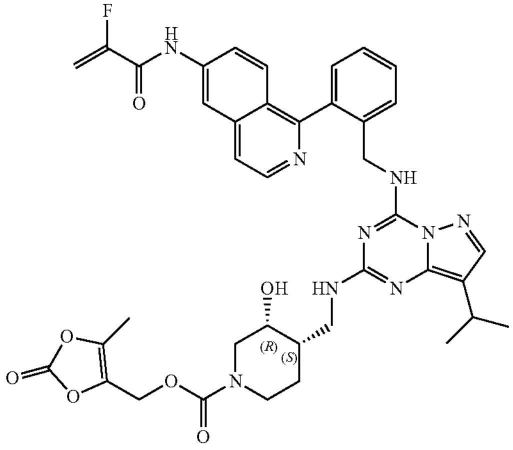 |
| 14 | 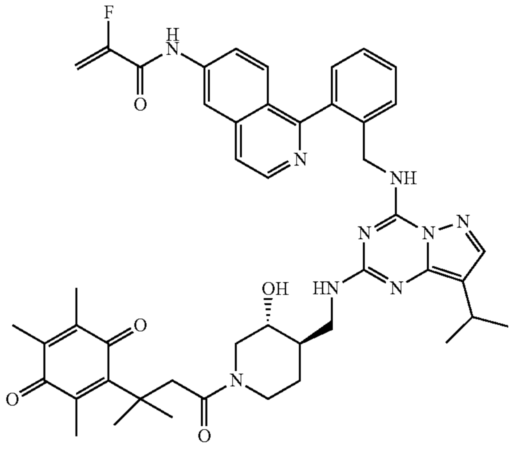 [SMILES: C=C(F)C(=O)Nc1ccc2c(-c3ccccc3CNc3nc(NC[C@H]4CCN(C(=O)CC(C)(C)C5=C(C)C(=O)C(C)=C(C)C5=O)C[C@@H]4O)nc4c(C(C)C)cnn34)nccc2c1] |
| 15 | 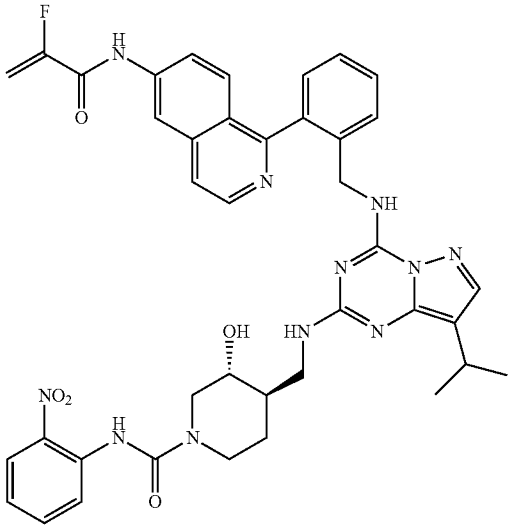 [SMILES: C=C(F)C(=O)Nc1ccc2c(-c3ccccc3CNc3nc(NC[C@H]4CCN(C(=O)Nc5ccccc5[N+](=O)[O-])C[C@@H]4O)nc4c(C(C)C)cnn34)nccc2c1] |
-continued
| No. | compound |
|---|---|
| 16 | 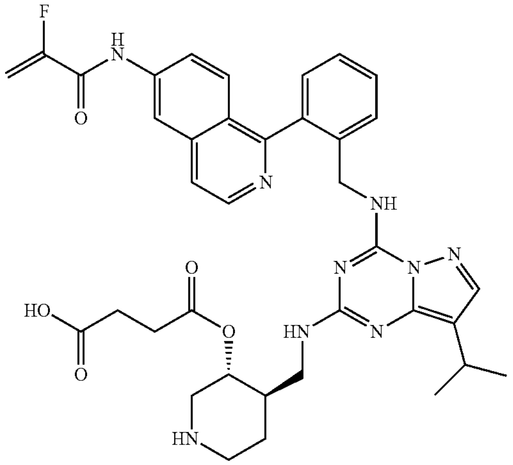 [SMILES: C=C(F)C(=O)Nc1ccc2c(-c3ccccc3CNc3nc(NC[C@H]4CCNC[C@@H]4OC(=O)CCC(=O)O)nc4c(C(C)C)cnn34)nccc2c1] |
| 17 | 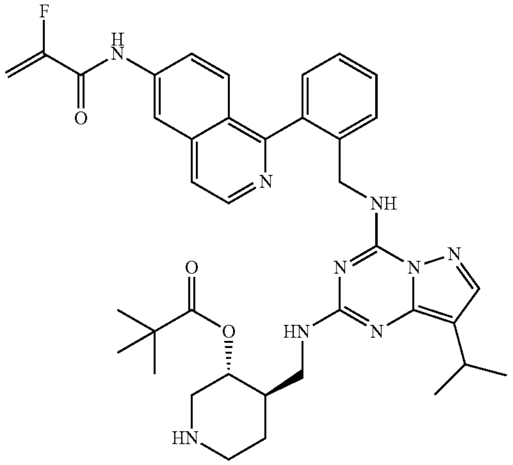 [SMILES: C=C(F)C(=O)Nc1ccc2c(-c3ccccc3CNc3nc(NC[C@H]4CCNC[C@@H]4OC(=O)C(C)(C)C)nc4c(C(C)C)cnn34)nccc2c1] |
| 18 | 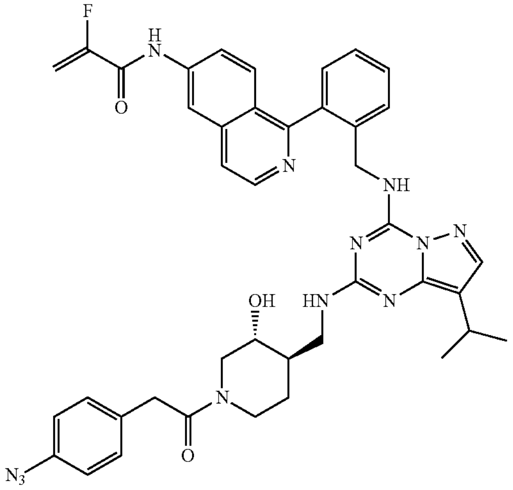 [SMILES: C=C(F)C(=O)Nc1ccc2c(-c3ccccc3CNc3nc(NC[C@H]4CCN(C(=O)Cc5ccc(N=[N+]=[N-])cc5)C[C@@H]4O)nc4c(C(C)C)cnn34)nccc2c1] |

-continued

| No. | compound |
|---|---|
| 19 | 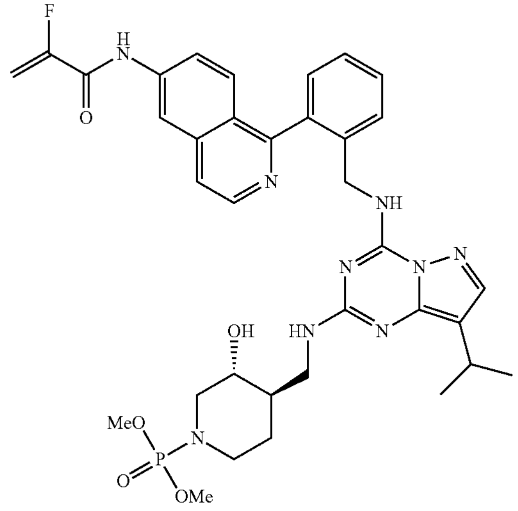 [SMILES: C=C(F)C(=O)Nc1ccc2c(-c3ccccc3CNc3nc(NC[C@H]4CCN(P(=O)(OC)OC)C[C@@H]4O)nc4c(C(C)C)cnn34)nccc2c1] |
| 20 | 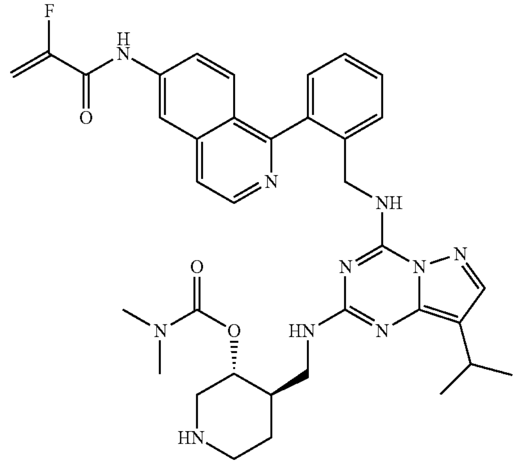 [SMILES: C=C(F)C(=O)Nc1ccc2c(-c3ccccc3CNc3nc(NC[C@H]4CCNC[C@@H]4OC(=O)N(C)C)nc4c(C(C)C)cnn34)nccc2c1] |

or an enantiomer, stereoisomeric form, mixture of enantiomers, diastereomer, mixture of diastereomers, racemate of the above mentioned compounds or a pharmaceutically acceptable salt thereof.

5. A pharmaceutical composition comprising a compound according to claim 1, together with at least one pharmaceutically acceptable carrier, excipient and/or diluent.

6. The pharmaceutical composition according to claim 5, formulated for oral administration.

7. A method for prevention and/or treatment of a disease that is associated with inhibition of apoptosis, abnormal transcriptional activity and/or cell cycle arrest by aberrant activity and/or overexpression of one or several cyclin-dependent kinases (CDKs), wherein said method comprises administering, to a subject in need of such prevention and/or treatment, a compound according to claim 1.

8. The method according to claim 7, wherein the disease is a proliferative disease selected from the group consisting of: adenocarcinoma, choroidal melanoma, acute leukemia, acoustic neurinoma, ampullary carcinoma, anal carcinoma, astrocytoma, basal cell carcinoma, pancreatic cancer, Desmoid tumor, bladder cancer, bronchial carcinoma, estrogen dependent and independent breast cancer, Burkitt's lymphoma, corpus cancer, Carcinoma unknown primary tumor (CUP-syndrome), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic tumor, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymphomas, stomach cancer, malignant melanoma, malignant neoplasia, malignant tumors gastrointestinal tract, breast carcinoma, rectal cancer, medulloblastomas, melanoma, meningiomas, Hodgkin's/Non-Hodgkin's lymphoma, mycosis fungoides, nasal cancer, neurinoma, neuroblastoma, kidney cancer, renal cell carcinomas, oligodendroglioma, esophageal carcinoma, osteolytic carcinomas and osteoplastic carcinomas, osteosarcomas, ovarian carcinoma, pancreatic carcinoma, penile cancer, plasmacytoma, prostate cancer, pharyngeal cancer, rectal carcinoma, retinoblastoma, vaginal cancer, thyroid carcinoma, esophageal cancer, T-cell lymphoma, thymoma, tube carcinoma, eye tumors, urethral cancer, urologic tumors, urothelial carcinoma, vulva cancer, wart appearance, soft tissue tumors, soft tissue sarcoma, Nephroblastoma, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypothalamic glioma, cerebellar astrocytoma, cerebral astrocytoma, neuroectodermal tumor, pineal tumors, sarcoma of the uterus, salivary gland cancers, anal gland adenocarcinomas, mast cell tumors, pelvis tumor, ureter tumor, hereditary papillary renal cancers, sporadic papillary renal cancers, intraocular melanoma, hepatocellular carcinoma, cholangiocarcinoma, mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-cell lymphoma, lymphoma of the central nervous system, malignant fibrous histiocytoma, lymph sarcoma, rhabdomyosarcoma, malignant histiocytosis, fibroblastic sarcoma, hemangiosarcoma, hemangiopericytoma, leiomyosarcoma (LMS), canine mammary carcinoma, and feline mammary carcinoma.

9. The method according to claim 7, wherein the disease is an infectious disease selected from the group consisting of AIDS, Adenovirus Infection, Alveolar Hydatid Disease (AID), Amoebiasis, Angiostrongyliasis, Anisakiasis, Anthrax, Babesiosis, Balantidiasis, *Baylisascaris* Infection, *Bilharzia* (Schistosomiasis), *Blastocystis hominis* Infection, Lyme Borreliosis, Botulism, Brainerd Diarrhea, Brucellosis, Bovine Spongiform Encephalopathy (BSE), Candidiasis, Capillariasis, Chronic Fatigue Syndrome (CFS), Chagas Disease, Chickenpox, *Chlamydia pneumoniae* Infection, Cholera, Chronic Fatigue Syndrome, Creutzfeldt-Jakob Disease (CJD), Clonorchiasis, Cutaneous Larva migrans (CLM), Coccidioidomycosis, Conjunctivitis, Coxsackievirus A16 (Cox A16), Cryptococcal disease, Cryptosporidiosis, West Nile fever, Cyclosporiasis, Neurocysticercosis, Cytomegalovirus Infection, Dengue Fever, *Dipylidium caninum* Infection, Ebola Hemorrhagic Fever (EIF), Alveolar Echinococcosis (AE), Encephalitis, *Entamoeba coli* Infection, *Entamoeba dispar* Infection, *Entamoeba hartmanni* Infection, *Entamoeba polecki* Infection, Pinworm Infection, Enterovirus Infection (Polio/Non-Polio), Epstein Barr Virus Infection, *Escherichia coli* Infection, Foodborne Infection, Aphthae epizooticae, Fungal Dermatitis, Fungal Infections, Gastroenteritis, Group A streptococcal Disease, Group B streptococcal Disease, Hansen's Disease (Leprosy), Hantavirus Pulmonary Syndrome, 1-lead Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis, Lassa Fever, Leishmaniasis, Visceral leishmaniasis (VL), Malaria, Marburg Hemorrhagic Fever, Measles, Meningitis, *Mycobacterium avium* Complex (MAC) Infection, *Naegleria* Infection, Nosocomial Infections, Nonpathogenic Intestinal Amebae Infection, Onchocerciasis, Opisthorchiasis, Papilloma virus Infection, Parvovirus Infection, Plague, *Pneumocystis* Pneumonia (PCP), Polyomavirus Infection, Q Fever, Rabies, Respiratory Syncytial Virus (RSV) Infection, Rheumatic Fever, Rift Valley Fever, Rotavirus Infection, Roundworms Infection, *Salmonellosis*, Scabies, Shigellosis, Shingles, Sleeping Sickness, Smallpox, Streptococcal Infection, Tapeworm Infection, Tetanus, Toxic Shock Syndrome, Tuberculosis, duodenum, *Vibrio parahaemolyticus* Infection, *Vibrio* septicemia, Viral Hemorrhagic Fever, Warts, Waterborne infectious Diseases, Varicella-Zoster Virus infection, Pertussis and Yellow Fever.

10. The method according to claim 7, wherein the disease is an immunological disease and/or autoimmune disease selected from the group consisting of: asthma, diabetes, rheumatic diseases, AIDS, rejection of transplanted organs and tissues, rhinitis, chronic obstructive pulmonary diseases, osteoporosis, ulcerative colitis, sinusitis, lupus erythematosus, recurrent infections, atopic dermatitis/eczema and occupational allergies, food allergies, drug allergies, severe anaphylactic reactions, anaphylaxis, manifestations of allergic diseases, primary immunodeficiencies, antibody deficiency states, cell mediated immunodeficiencies, severe combined immunodeficiency, DiGeorge syndrome, Hyper IgE syndrome (HIES), Wiskott-Aldrich syndrome (WAS), ataxia-telangiectasia, immune mediated cancers, white cell defects, autoimmune diseases, systemic lupus erythematosus (SLE), rheumatoid arthritis (RA), multiple sclerosis (MS), immune-mediated or Type 1 Diabetes Mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, Hashimoto's disease, dermatomyositis, Goodpasture syndrome (GPS), myasthenia gravis (MG), Sympathetic ophthalmia, Phakogene Uveitis, chronical aggressive hepatitis, primary biliary cirrhosis, autoimmune hemolytic anemia and Werlhof's disease.

11. The method according to claim 7, wherein the disease is an inflammatory disease that is caused, induced, initiated and/or enhanced by bacteria, viruses, prions, parasites, fungi, and/or is caused by irritative, traumatic, metabolic, allergic, autoimmune, or idiopathic agents.

12. The method according to claim 7, wherein the disease is an inflammatory disease selected from the group consisting of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, and inflammatory diseases of the larynx.

13. The method according to claim 7, wherein the disease is an inflammatory disease selected from inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflamatory disease uveitis, inflammatory diseases of the larynx, wherein preferably said inflammatory diseases are selected from the group comprising abscessation, acanthamoeba infection, acne vulgaris, actinomycosis, acute inflammatory dermatoses, acute laryngeal infections of adults, acute multifocal placoid pigment epitheliopathy, acute (thermal) injury, acute retinal necrosis, acute suppurative otitis media, algal disorders, allergic contact dermatitis, amyloidosis angioedema, ankylosing spondylitis, aspergillosis, atopic dermatitis, pseudorabies, autoantibodies in vasculitis, bacterial disorders, bacterial laryngitis, bacterial meningitis, Behçet's disease (BD), birdshot choroidopathy, Gilchrist's disease, Borna disease, brucellosis, bullous myringitis, bursitis, candidiasis, canine distemper encephalomyelitis, canine distemper encephalomyelitis in immature animals, canine hemorrhagic fever, canine herpes virus encephalomyelitis, cholesteatoma, chronic granulomatous diseases (CGD), chronic inflammatory dermatoses, chronic relapsing encephalomyelitis, chronic suppurative otitis media, Ocular Cicatricial pemphigoid (OCP), common upper respiratory infection, granuloma, Crohn's disease, cryptococcal disease, dermatomyositis, diphtheria, discoid lupus erythematosus (DLE), drug-induced vasculitis, drug or hypersensitivity reaction, encephalitozoonosis, eosinophilic meningoencephalitis, Erythema multiforme (EM), feline leukemia virus, feline immunodeficiency virus, feline infectious peritonitis, feline Polioencephalitis, feline spongiform encephalopathy, fibromyalgia, Fuchs Heterochromic Uveitis, gastroesophageal (laryngopharyngeal) reflux disease, giant cell arteritis, glanders, glaucomatocyclitic crisis, gonorrhea granular myringitis, Granulomatous meningoencephalitis (GME), herpes simplex, histoplasmosis, idiopathic diseases, idiopathic inflammatory disorders, immune and idiopathic disorders, infections of the immunocompromised host, infectious canine hepatitis, inhalation laryngitis, interstitial nephritis, irritant contact dermatitis, juvenile rheumatoid arthritis, Kawasaki's disease, La Crosse virus encephalitis, laryngeal abscess, laryngotracheobronchitis, leishmaniasis, lens-induced uveitis, leprosy, leptospirosis, leukemia, lichen planus, lupus, lymphoma, meningitis, meningoencephalitis in greyhounds, miscellaneous meningitis/meningoencephalitis, microscopic polyangiitis, multifocal choroiditis, multifocal distemper encephalomyelitis in mature animals, multiple sclerosis, Muscle Tension Dysphonia (MTD), mycotic (fungal) diseases, mycotic diseases of the CNS, necrotizing encephalitis, neosporosis, old dog encephalitis, onchocerciasis, parasitic encephalomyelitis, parasitic infections, Pars planitis, parvovirus encephalitis, pediatric laryngitis, pollution and inhalant allergy, polymyositis, post-vaccinal canine distemper encephalitis, prion protein induced diseases, protothecosis, protozoal encephalitis-encephalomyelitis, psoriasis, psoriatic arthritis, pug dog encephalitis, radiation injury, radiation laryngitis, radionecrosis, relapsing polychondritis, Reiter's syndrome, retinitis pigmentosa, retinoblastoma, rheumatoid arthritis, Rickettsial disorders, rocky mountain spotted fever, salmon poisoning disease (SPD), Sarcocystosis, sarcoidosis, schistosomiasis, sclerodenna, Rhinoscleroma, serpiginous choroiditis, shaker dog disease, Sjogren's syndrome, spasmodic croup, spirochetal (syphilis) diseases, spongiotic dermatitis, sporotrichosis, steroid responsive meningitis-arteritis, Stevens-Johnson syndrome (SJS, EM major), epiglottitis, sympathetic ophthalmia, Syngamosis, syphilis, systemic vasculitis in sarcoidosis, Takayasu's arteritis, tendinitis (tendonitis), Thromboangiitis obliterans (Buerger Disease), tick-borne encephalitis in dogs, toxic epidermal necrolysis (TEN), toxocariasis, toxoplasmosis, trauma, traumatic laryngitis, trichinosis, trypanosomiasis, tuberculosis, tularemia, ulcerative colitis, urticaria (hives), vasculitis, vasculitis and malignancy, vasculitis and rheumatoid arthritis, vasculitis in the idiopathic inflammatory myopathies, vasculitis of the central nervous system, vasculitis secondary to bacterial, fungal, and parasitic infection, viral disorders, viral laryngitis, vitiligo, vocal abuse, vocal-cord hemorrhage, Vogt-Koyanagi-Harada syndrome (VKH), Wegener's granulomatosis, and Whipple's disease.

14. The compound according to claim 4, wherein said compound is any one of the compounds 2, 3, 4, 5, 6, and 8; or an enantiomer, stereoisomeric form, mixture of enantiomers, diastereomer, mixture of diastereomers, racemate of the above mentioned compounds or a pharmaceutically acceptable salt thereof.

15. The compound according to claim 4, wherein said compound is any one of the compounds 2, 3, 4, 5 and 6; or an enantiomer, stereoisomeric form, mixture of enantiomers, diastereomer, mixture of diastereomers, racemate of the above mentioned compounds or a pharmaceutically acceptable salt thereof.

16. The compound according to claim 4, wherein said compound is compound 3; or an enantiomer, stereoisomeric form, mixture of enantiomers, diastereomer, mixture of diastereomers, racemate of the above mentioned compounds or a pharmaceutically acceptable salt thereof.

* * * * *